US008796252B2

(12) United States Patent
Rioux et al.

(10) Patent No.: US 8,796,252 B2
(45) Date of Patent: Aug. 5, 2014

(54) PYRITHIONE BIOCIDES ENHANCED BY ZINC METAL IONS AND ORGANIC AMINES

(75) Inventors: Michelle L. Rioux, Middletown, CT (US); Diana T. Ciccognani, Cheshire, CT (US); Thomas J. Palys, Cascade, MD (US); Patricia A. Turley, Orange, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 711 days.

(21) Appl. No.: 11/020,954

(22) Filed: Dec. 23, 2004

(65) Prior Publication Data

US 2005/0158263 A1    Jul. 21, 2005

Related U.S. Application Data

(60) Division of application No. 10/325,016, filed on Dec. 20, 2002, now Pat. No. 6,908,912, which is a continuation-in-part of application No. 09/599,371, filed on Jun. 22, 2000, now Pat. No. 7,455,851.

(60) Provisional application No. 60/141,195, filed on Jun. 25, 1999.

(51) Int. Cl.
*A01N 55/02* (2006.01)
*A61K 31/555* (2006.01)

(52) U.S. Cl.
USPC ........................................................ 514/188

(58) Field of Classification Search
USPC ........................................................ 514/188
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,786,847 A | 3/1957 | Cislak .................. 260/294.8 |
| 2,798,053 A | 7/1957 | Brown |
| 2,809,971 A | 10/1957 | Bernstein et al. ............. 260/270 |
| 2,826,551 A | 3/1958 | Geen |
| 2,951,789 A | 9/1960 | McCants |
| 3,152,046 A | 10/1964 | Kapral |
| 3,155,591 A | 11/1964 | Hilfer |
| 3,159,640 A | 12/1964 | McClure et al. ........... 260/294.8 |
| 3,236,733 A | 2/1966 | Karsten et al. ................ 167/87 |
| 3,332,880 A | 7/1967 | Kessler |
| 3,589,999 A | 6/1971 | McRae et al. ................... 210/28 |
| 3,590,035 A | 6/1971 | Damico ........................ 260/290 |
| 3,636,213 A | 1/1972 | Gerstein et al. ............... 424/245 |
| 3,753,196 A | 8/1973 | Kurtz et al. |
| 3,761,418 A | 9/1973 | Parran |
| 3,773,770 A | 11/1973 | Damico ........................ 260/290 |
| 3,852,441 A | 12/1974 | Kooistra, Jr. .................. 424/245 |
| 3,929,678 A | 12/1975 | Laughlin et al. |
| 3,940,482 A * | 2/1976 | Grand ........................... 514/188 |
| 3,958,581 A | 5/1976 | Abegg et al. |
| 3,959,461 A | 5/1976 | Bailey et al. |
| 3,960,782 A | 6/1976 | Daley et al. |
| 3,964,500 A | 6/1976 | Drakoff |
| 4,055,655 A | 10/1977 | Maurer et al. ................ 424/294 |
| 4,089,945 A | 5/1978 | Brinkman et al. |
| 4,152,416 A | 5/1979 | Spitzer et al. |
| 4,161,526 A | 7/1979 | Gorman ........................ 424/245 |
| 4,197,865 A | 4/1980 | Jacquet et al. |
| 4,217,914 A | 8/1980 | Jacquet et al. |
| 4,235,873 A | 11/1980 | Packman ........................ 424/47 |
| 4,323,683 A | 4/1982 | Bolich, Jr. et al. |
| 4,345,080 A | 8/1982 | Bolich, Jr. |
| 4,364,387 A | 12/1982 | Larkin |
| 4,370,325 A | 1/1983 | Packman ...................... 424/245 |
| 4,374,852 A | 2/1983 | Hilditch et al. |
| 4,379,753 A | 4/1983 | Bolich, Jr. |
| 4,381,919 A | 5/1983 | Jacquet et al. |
| 4,387,090 A | 6/1983 | Bolich, Jr. |
| 4,422,853 A | 12/1983 | Jacquet et al. |
| 4,454,153 A | 6/1984 | Lowicki et al. |
| 4,470,982 A | 9/1984 | Winkler |

(Continued)

FOREIGN PATENT DOCUMENTS

| | | | |
|---|---|---|---|
| CA | 1 264 671 | 1/1990 | ............... A61K 7/48 |
| CA | 2 132 170 | 3/1996 | ............... A61K 7/06 |

(Continued)

OTHER PUBLICATIONS

CAS accession No. 1989:4523435 corresponding to Kuznowski et. al., Tribologia (1988) 19: 20-21.*
Kaznowski et. al. (CAS accession No. 1989:452345 corresponding to Tribologia (1988) 19: 20-21).*
Kaznowski et. al. (Tribologia (1988) 19:20-21).*
Kaznowski et. al. (Tribologia (1988) 19: 20-21).*
E. O. Bennet et al., "The Effects of Metals Upon the Inhibitory Activities of Cutting Fluid Preservatives", International Biodeterioration Bulletin ISSN 0020-6164 18[1] (1982), pp. 7-12.
H. Akiyama et al., "Effects of zinc oxide on the attachment of *Staphylococcus aureus* strains", Journal of Dermatological Science 17 (1998), pp. 67-74.
Article by M. M. Khattar et al., entitled "Aspects of the mode of action of pyrithione against *Klebsiella pneumoniae*", Journal of Antimicrobial Chemotherapy (1993) 5(S1), pp. 175-177.
Saxton, Charles A. et al., "Antiplaque effects and mode of action of a combination of zinc citrate and a nonionic antimicrobial agent", Scandinavian Journal of Dental Research, Jun. 1988, p. 212-217, vol. 96, No. 3, XP-001079620, Copenhagen, Denmark.

(Continued)

*Primary Examiner* — Marcos Sznaidman
(74) *Attorney, Agent, or Firm* — Miles & Stockbridge P.C.

(57) ABSTRACT

The present invention is directed to a stable, soluble, antimicrobial composition concentrate comprising pyrithione or a pyrithione complex in an amount of from about 0.5% to about 30 weight percent, a zinc source in an amount of from about 0.1% to about 10%, and an organic amine component in an amount of from about 30% to about 80%, said percents being based upon the total weight of the composition concentrate. The invention is also directed to methods of controlling the growth of free-living microorganisms or biofilms using the antimicrobial composition of the invention, and products made using the antimicrobial composition of the invention.

7 Claims, No Drawings

(56) References Cited

U.S. PATENT DOCUMENTS

| | | | |
|---|---|---|---|
| 4,507,280 A | 3/1985 | Pohl et al. | |
| 4,529,586 A | 7/1985 | De Marco et al. | |
| 4,608,183 A | 8/1986 | Rossmoore | 252/36 |
| 4,654,213 A | 3/1987 | Ramirez et al. | 424/145 |
| 4,663,158 A | 5/1987 | Wolfram et al. | |
| 4,666,616 A | 5/1987 | Rossmoore | 252/11 |
| 4,670,430 A | 6/1987 | Imamura et al. | |
| 4,686,254 A | 8/1987 | Lochhead et al. | |
| 4,704,272 A | 11/1987 | Oh et al. | |
| 4,788,006 A | 11/1988 | Bolich, Jr. et al. | |
| 4,818,436 A * | 4/1989 | French et al. | 252/400.23 |
| 4,834,767 A | 5/1989 | Helioff et al. | |
| 4,835,149 A * | 5/1989 | Burke et al. | 514/188 |
| 4,885,107 A | 12/1989 | Wetzel | |
| 4,898,585 A | 2/1990 | Borsanyi et al. | |
| 4,925,582 A * | 5/1990 | Bennett | 508/248 |
| 4,933,101 A | 6/1990 | Cilley et al. | |
| 4,943,432 A | 7/1990 | Biener | |
| 5,057,153 A | 10/1991 | Ruggiero | 106/18.33 |
| 5,104,645 A | 4/1992 | Cardin et al. | |
| 5,104,646 A | 4/1992 | Bolich, Jr. et al. | |
| 5,106,609 A | 4/1992 | Bolich, Jr. et al. | |
| 5,114,984 A | 5/1992 | Branch et al. | 521/121 |
| 5,120,831 A | 6/1992 | Pickart | 530/331 |
| 5,202,048 A | 4/1993 | Bartolo et al. | |
| 5,227,156 A | 7/1993 | Wiese | 424/70 |
| 5,246,489 A | 9/1993 | Farmer, Jr. et al. | 106/18.33 |
| 5,284,649 A | 2/1994 | Juneja | |
| RE34,584 E | 4/1994 | Grote | |
| 5,462,589 A | 10/1995 | Nicholas et al. | 106/18.33 |
| 5,478,501 A | 12/1995 | Rau | |
| 5,518,774 A * | 5/1996 | Kappock et al. | 427/384 |
| 5,540,954 A | 7/1996 | Nicholas et al. | 427/397 |
| 5,562,995 A | 10/1996 | Kappock et al. | 428/469 |
| 5,580,494 A | 12/1996 | Sandhu et al. | |
| 5,614,538 A | 3/1997 | Nelson, Jr. | 514/345 |
| 5,674,478 A | 10/1997 | Dodd et al. | |
| 5,696,169 A | 12/1997 | Otsu et al. | |
| 5,716,628 A * | 2/1998 | Vinopal et al. | 424/405 |
| 5,723,112 A | 3/1998 | Bowser et al. | |
| 5,750,122 A | 5/1998 | Evans et al. | |
| 5,798,121 A | 8/1998 | Cauwet et al. | |
| 5,837,661 A | 11/1998 | Evans et al. | |
| 5,854,266 A | 12/1998 | Nelson, Jr. | 514/345 |
| 5,854,319 A | 12/1998 | O'Lenick, Jr. et al. | |
| 5,874,476 A | 2/1999 | Hsu et al. | 514/640 |
| 5,880,076 A | 3/1999 | Vermeer | 510/123 |
| 5,883,085 A | 3/1999 | Blank et al. | |
| 5,883,154 A * | 3/1999 | Kappock et al. | 523/122 |
| 5,939,203 A | 8/1999 | Kappock et al. | |
| 5,965,515 A | 10/1999 | Rau | |
| 6,017,562 A | 1/2000 | Kaufman et al. | 424/489 |
| 6,034,043 A | 3/2000 | Fujiwara et al. | 510/130 |
| 6,333,040 B1 | 12/2001 | Boyxen et al. | |
| RE37,793 E | 7/2002 | Domenico | |
| 6,495,538 B2 | 12/2002 | Fliss | |
| 6,534,788 B1 | 3/2003 | Yeo et al. | |
| 6,649,585 B1 | 11/2003 | Daute et al. | |
| 6,774,096 B1 | 8/2004 | Paye | |
| 6,908,912 B2 | 6/2005 | Rioux et al. | |
| 2003/0030042 A1 | 2/2003 | Sawada et al. | |
| 2003/0044471 A1 | 3/2003 | Sakuma et al. | |
| 2003/0119805 A1 | 6/2003 | Fliss | |
| 2003/0215522 A1 | 11/2003 | Johnson et al. | |
| 2004/0058855 A1 | 3/2004 | Schwartz et al. | |
| 2004/0167114 A1 | 8/2004 | Fliss | |
| 2004/0191331 A1 | 9/2004 | Schwartz et al. | |
| 2004/0213751 A1 | 10/2004 | Schwartz et al. | |
| 2004/0223941 A1 | 11/2004 | Schwartz et al. | |
| 2005/0202984 A1 | 9/2005 | Schwartz et al. | |
| 2006/0024381 A1 | 2/2006 | Schwartz et al. | |
| 2006/0046943 A1 | 3/2006 | Erazo-Majewicz et al. | |
| 2007/0128147 A1 | 6/2007 | Schwartz et al. | |

FOREIGN PATENT DOCUMENTS

| | | | |
|---|---|---|---|
| EP | 37318 A1 | 10/1981 | |
| EP | 0 077 630 | 4/1983 | A61K 7/06 |
| EP | 0589047 A1 | 3/1994 | |
| EP | 1145707 A1 | 10/2001 | |
| EP | 1161869 A1 | 12/2001 | |
| FR | 2478467 A1 | 9/1981 | |
| FR | 2593801 A1 | 8/1987 | |
| GB | 761171 | 5/1954 | |
| GB | 2141929 A | 1/1985 | |
| GB | 2 230 190 A | 10/1990 | A01N 43/80 |
| JP | 60-174707 | 9/1985 | A61K 7/06 |
| JP | 61236708 A | 10/1986 | |
| JP | 69352 | 1/1994 | |
| JP | 6-134227 | 5/1994 | B01D 39/14 |
| JP | 6-256689 | 9/1994 | C09D 5/14 |
| JP | 6296402 A | 10/1994 | |
| JP | 07053369 A | 2/1995 | |
| JP | 7-118103 | 5/1995 | A01N 25/00 |
| JP | 9175984 A | 7/1997 | |
| JP | 10510290 A | 10/1998 | |
| JP | 10328280 A | 12/1998 | |
| JP | 11228368 A | 8/1999 | |
| KR | 1997-01014 | 3/1997 | |
| WO | 9410973 A1 | 5/1994 | |
| WO | 9534524 A1 | 12/1995 | |
| WO | WO 9610387 | 4/1996 | A61K 7/06 |
| WO | 9625913 A1 | 8/1996 | |
| WO | WO 9806260 | 2/1998 | A01N 25/08 |
| WO | 9847372 A1 | 10/1998 | |
| WO | WO 99/21568 | 5/1999 | A61K 33/24 |
| WO | WO 9921568 | 5/1999 | A61K 33/24 |
| WO | 9959540 A1 | 11/1999 | |
| WO | WO 0006100 | 2/2000 | A61K 7/06 |
| WO | 0100021 A1 | 1/2001 | |
| WO | 0100151 A1 | 1/2001 | |
| WO | 0141727 A1 | 6/2001 | |
| WO | 0151418 A1 | 7/2001 | |
| WO | 0193817 A1 | 12/2001 | |
| WO | 0232381 A2 | 4/2002 | |
| WO | 02076422 A2 | 10/2002 | |
| WO | 02080943 A1 | 10/2002 | |
| WO | 03088957 A1 | 10/2003 | |
| WO | 03088965 A1 | 10/2003 | |

OTHER PUBLICATIONS

Encyclopedia of Polymer Science and Engineering, 1989, pp. 204-308, vol. 15, Second Edition, John Wiley & Sons, Inc.

D. J. Burgess, "Practical Analysis of Complex Coarcervate Systems," Journal of Colloid and Interface Science, Nov. 1990, pp. 227-238, vol. 140, No. 1, Academic Press, Inc.

Van Oss, C. J., "Coacervation, Complex-Coacervation and Flocculation", J. Dispersion science and Technology, 1989, pp. 561-573, vol. 9 (5,6). Marcel Dekker, Inc.

BASF, "Z-Cote microfine zinc oxide", xP-002287832, 2000, p. 1-7.

Van Cutsem, J. et. al., xP-002288119, Journal of the American Academy of Dermatology, 1989, vol. 22, No. 61, p. 993-998, Amsterdam.

MSDS Mallinckrodt Baker, Inc. Zinc Carbonate Feb. 16, 2006 pp. 1-7.

Hwang, Sung-Ho, et. al., Intercalation of Functional organic Molecules with Pharmaceutical, Cosmecutical and Nutraceutical Functions into Layered Double Hydroxides and Zinc Basic Salts.

Louer et. al., Chemistry of Materials, 1998, 10, 2450-2461.

Kravzov et. al., Journal of Applied Toxicology, 1993, 13(3), 213-216, Abstract only.

McMurry, John, organic Chemistry, 2nd Edition, Brooks-Cole Publishing Company, p. 1010 (1988).

The Mineral Willemite [online] retrieved from the internet on Nov. 26, 2007 retrieved from http://www.galleries.com/minerals/silicate/willemit/willemit.htm 2 pages.

Willemite [online] retrieved from the internet http://www.mindat.org/min-4292.html retrieved on Nov. 26, 2007; pp. 1-16.

* cited by examiner

PYRITHIONE BIOCIDES ENHANCED BY ZINC METAL IONS AND ORGANIC AMINES

This application is a divisional of application Ser. No. 10/325,016, filed on Dec. 20, 2002, issued as U.S. Pat. No. 6,908,912, which is a continuation-in-part application Ser. No. 09/599,371, filed on Jun. 22, 2000, issued as U.S. Pat. No. 7,455,851, which claims the benefit of Provisional Application Ser. No. 60/141,195, filed on Jun. 25, 1999. Ser. Nos. 10/325,016; 09/599,371 and 60/141,195 are all incorporated by reference in their entireties herein.

BACKGROUND OF THE INVENTION

1. Field of the Invention

The present invention is directed to pyrithione biocides, and more particularly to a stable, soluble biocidal composition displaying an enhanced biocidal effect, comprising an antimicrobially effective combination of pyrithione, pyrithione salt, or pyrithione adduct, a zinc source such a zinc alloy, zinc oxide, zinc hydroxide, or zinc salt, and 1,2-1,3 alkanolamines and 1,2-1,3-alkyldiamines. The biocidal composition is provided in the form of a biocidal composition concentrate that is suitably incorporated directly into a functional fluid (such as a metalworking fluid) or incorporated into a functional fluid "masterbatch".

2. Brief Description of the Related Art

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents, and are widely used as fungicides and bacteriocides in paints and metalworking fluids. Pyrithiones are also used as fungicides and bacteriocides in personal care products such as anti-dandruff shampoos. The polyvalent metal salts of pyrithione are only sparingly soluble in water and include ferric pyrithione, ferrous pyrithione, aluminum pyrithione, bismuth pyrithione, strontium pyrithione, copper pyrithione, zinc pyrithione, cadmium pyrithione, and zirconium pyrithione. The most widely used divalent pyrithione salts are zinc pyrithione and copper pyrithione.

Zinc and copper pyrithione are useful as antimicrobial agents active against gram-positive and negative bacteria, fungi, and yeasts. Zinc pyrithione is used as an antidandruff component in shampoos, while technical suspensions of zinc pyrithione and/or copper pyrithione are used as preservatives in paints and polymers. Powders of these same salts are also used as cobiocides in antifouling paints. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589,999; 3,590,035; 3,773,770.

While pyrithione biocides have proven useful for a wide range of applications as outlined above, the utility of these compounds is limited to the control of select species and strains of fungi and bacteria. Further, while higher concentrations of pyrithione or its salts have been observed to control the growth of a wider range of organisms, the useful amount of pyrithione or its salts that can be added to a commercial product is limited by efficacy and economic considerations, and, to a lesser extent, environmental and toxicological concerns.

Inorganic salts of zinc such as zinc chloride, zinc sulfate, and zinc oxide, have been employed as a bacteriostatic and/or fungistatic compounds in a large variety of products including paints, coatings, and antiseptics. However, while zinc salts are less toxic than pyrithione or its salts, these compounds do not possess the high biocidal efficacy that is desired in many commercial applications.

Certain combinations of pyrithione and zinc are known in the art. Illustratively, U.S. Pat. Nos. 5,854,266 and 5,883,154 disclose an aqueous antimicrobial composition protected against discoloration attributable to the presence of ferric ion or cupric ion therein, wherein the composition comprises pyrithione and a discoloration-inhibiting amount (between 0.001% to 10%) of a zinc compound selected from the group consisting of zinc salts of organic acids, zinc salts of inorganic acids, zinc hydroxide, zinc oxide, and combinations thereof. However, this patent does not describe any advantageous antimicrobial effects between pyrithione and zinc. Furthermore, at the concentrations employed in the patent, the compositions of pyrithione and zinc would not be soluble and thus could not be delivered together as a soluble biocidal composition. In another illustration, U.S. Pat. No. 4,161,526 discloses a white to cream yellow pyrithione salt or dipyrithione for application to skin or hair containing 0.01% to 1% of the zinc salt of an organic or inorganic acid, zinc hydroxide, zinc oxide, or combinations thereof. However, this patent does not describe any advantageous effect between pyrithione and the zinc salt nor would it form a soluble composition of pyrithione and zinc.

While bacteria and fungi have presented microbial contamination problems for many years, biofilms have recently been appreciated as a significant new source of microbial contamination. Biofilms are generally characterized as aggregates of cells adhered to one another or to surfaces by an extracellular layer of slime. Biofilms are commonly found as contaminants in metalworking fluids because these fluids contain good carbon sources for growth of the organisms that are found in biofilms. However, high concentrations of biofilms in metalworking fluid result in rapid deterioration of the fluid, and can cause equipment problems and failure.

The growth of biofilms on surfaces can also enhance the rates of corrosion of metal surfaces and degradation of paints, surface coatings and the construction materials underlying these coatings. On ship hulls, the presence of biofilms can lead to increased drag and may encourage colonization by larger invertebrate biofouling organisms. Biofilms are often responsible for both internal and cutaneous infections. The increased resistance of biofilms to antimicrobial treatments often make biofilm-related infections more difficult to treat. Medical devices, such as cardiac implants and catheters, and medical instruments, such as dialysis machines and dental waterlines also become contaminated by biofilms and can spread infection.

While previous efforts have been made to control the growth and proliferation of biofilms, these efforts have met with only limited success. Research has indicated that biofilm cells are much more resistant to disinfection than free-living cells, due in large part to the extracellular slime layer which acts as a protective coating. Moreover, strategies to control microbial contamination heretofore were typically developed in the laboratory against free-living organisms, and little or no attention was given towards determining the effectiveness of antimicrobial agents against biofilm. Unfortunately, the resistant biofilms are generally not affected by previously employed antimicrobials. If not removed or destroyed, biofilms can cause a multitude of problems in functioning fluid applications, such as corrosion, clogging, slime build up on surfaces, foul odors, fluid instability, machine down-time, and the like.

Additional representative patents and publications showing the state of the art in the microbial disinfection area are as follows:

U.S. Pat. No. 4,654,213 discloses an antimicrobial composition in which a water-soluble salt of zinc enhances the activity of the $MgSO_4$ adduct of 2,2'-dithiopyridine-1,1'-dioxide (MDS).

U.S. Pat. No. 4,370,325 discloses a composition containing 2,2'-dithiopyridine-1,1'-dioxide or one of its metal salt adducts, including $MgSO_4$ (MDS) and Zn salts, for treating eye and ear irritation and inflammation.

U.S. Pat. No. 4,235,873 discloses a deodorant composition containing 2,2'-dithiopyridine-1,1'-dioxide or one of its metal salt adducts, including $MgSO_4$ (MDS) and Zn salts.

British Patent GB 2 230 190 A discloses a preservative composition containing an isothiazolone and the $ZnCl_2$ adduct of 2,2'-dithiopyridine-1,1'-dioxide. However, this patent does not describe any advantageous effect between pyrithione and the zinc salt.

Japanese patent application 6-134227 discloses an antibacterial filter incorporating ZnO or ZnO and zinc pyrithione. However, this patent does not describe any advantageous effect between pyrithione and the zinc salt.

Japanese patent application 7-118103 discloses an antimicrobial composition for coating stainless steel washing machine drums to prevent fouling of inner surfaces wherein ZnO is used as a carrier in a ZPT thermoplastic resin coating. However, this patent does not describe any advantageous effect between pyrithione and the zinc salt.

A technical journal article discloses that the presence of 0.2% metallic copper or 0.2% metallic zinc was found to decrease the biocidal activity of sodium pyrithione in 12 different metalworking fluids (E. O. Bennet et al. (1982) Int. Biodeterioration Bull. 18[1]: 7-12).

Another technical journal article (M. M. Khattar & W. G. Salt, Journal of Antimicrobial Chemotherapy (1993) 175-177) discloses the enhancement on the activity of pyrithione against *Klebsiella pnenmoniae* bacteria. More specifically, FIG. 2(a) of the Khattar & Salt article describes a favorable enhancement in the activity of 0.1% pyrithione against that bacteria that is attributable to the use of 0.01% of zinc chloride in combination with the pyrithione.

Copending patent application Ser. No. 09/599,371, filed on Jun. 22, 2000, discloses a biocidal composition comprising a combination of pyrithione, pyrithione salt, or pyrithione adduct, and a zinc or copper source, such as copper and/or zinc metal, oxide, hydroxide, or salt thereof. However, the antimicrobial compositions disclosed in this patent application will readily form insoluble precipitates as the concentrations of pyrithione and the zinc source are increased in the compositions, such as would be required to construct a concentrated biocidal composition (or "composition concentrate"). For example, compositions of pyrithione and zinc with concentrations greater than 0.0005% pyrithione and 0.00001% zinc will tend to form insoluble precipitates. These insoluble precipitates reduce the effectiveness of the composition as an antimicrobial agent, present problems for the long-term storage of a commercial product, and prohibit use where soluble biocides are required. Furthermore, the inability heretofore to construct a soluble, concentrated, biocidal composition of pyrithione and a zinc source necessitates the costly and inefficient administration of these components individually to applications, rather than in combination.

In addition, several patents have discussed solubilization of pyrithione derivatives with certain organic compounds.

U.S. Pat. No. 3,636,213 discloses solubilization of heavy metal salts of pyrithione (e.g., zinc pyrithione, copper pyrithione, and the like) using primary amines or polyalkyleneimines. However, this patent does not disclose any enhanced anti-microbial or anti-biofilm effect of the resulting solubilized pyrithione salts as compared to pyrithiones alone.

U.S. Pat. No. 3,940,482 discloses solubilization of heavy metal salts of pyrithione using long-chain polyamines for use in personal care products, such as soaps, shampoos, hairdressings, and the like. However, like the above patent, this patent does not disclose any improved or enhanced antimicrobial or anti-biofilm effect of the resulting solubilized pyrithione salts as compared to pyrithiones alone.

U.S. Pat. No. 4,835,149 discloses a method of solubilizing insoluble metal salts of pyrithione (such as zinc pyrithione, copper pyrithione, and the like) in the presence of certain amine compounds and certain aminocarboxylic acids. However, like the above patents, this patent does not disclose any improved or enhanced anti-microbial or anti-biofilm effect of the resulting solubilized pyrithione salts as compared to pyrithiones alone.

U.S. Pat. No. 5,114,984 discloses a process for imparting anti-bacterial and anti-fungal properties to a polyurethane foam by dissolving a pyrithione salt in an alkanolamine which is miscible in a polyol. However, like the above patents, this patent does not disclose any improved or enhanced antimicrobial or anti-biofilm effect of the resulting solubilized pyrithione salts as compared to pyrithiones alone.

Accordingly, what is needed in the art is a stable, soluble, concentrated biocidal composition of pyrithione, pyrithione salt, or pyrithione adduct, and a zinc source which permits the concurrent deliverance of high concentrations of pyrithione and zinc ions to an application, and which also offers an enhanced biocidal efficacy to pyrithione and its derivatives against free-living microorganisms and biofilms. Such a composition concentrate would be broadly useful, highly efficacious, cost-effective, and possess an enhanced biocidal effect both as an "in can" preservative and when diluted to form a "masterbatch" for use in a functional fluid, or when diluted directly into a functional fluid. The present invention is believed to be an answer to that need.

SUMMARY OF THE INVENTION

In one aspect, the present invention is directed to a stable, soluble, antimicrobial composition concentrate comprising pyrithione, pyrithione salt or a pyrithione complex in an amount of from about 0.05% to about 20 weight percent, a zinc source in an amount of from about 0.01% to about 5%, and an organic amine component in an amount of from about 30% to about 80%, said percents being based upon the total weight of the composition concentrate. The organic amine component comprises a first organic amine selected from the group consisting of 1,2-alkanolamines, and 1,3-alkanolamines, and combinations thereof, alone or in combination with a second organic amine selected from the group consisting of monomeric and polymeric forms of 1,2-alkyldiamines, monomeric and polymeric forms of 1,3-alkyldiamines, and combinations thereof. When the second organic amine is used, the first organic amine must be present in the antimicrobial composition concentrate in an amount sufficient to insure that the amine component is soluble in the antimicrobial composition concentrate. The antimicrobial composition concentrate advantageously can also contain a formaldehyde source in order to provide available formaldehyde in the antimicrobial composition concentrate. The antimicrobial composition concentrate of the present invention is suitably diluted to form a functional fluid "masterbatch", or it can be diluted directly into a functional fluid itself, as desired.

In another aspect, the present invention relates to a stable, soluble, antimicrobial composition made by diluting the above antimicrobial composition concentrate, and comprising:

from about 0.05% to about 5 wt % pyrithione or a pyrithione complex;

from about 0.005% to about 1 wt % of a zinc source selected from the group consisting of zinc salts, zinc oxides, zinc hydroxides, zinc borates, zinc sulfates, zinc chlorides, zinc alloys, zinc complexes, and combinations thereof; and from about 0.5% to about 40 wt % of an amine component comprising a first organic amine selected from the group consisting of 1,2-alkanolamines, and 1,3-alkanolamines, and combinations thereof, alone or in combination with a second organic amine selected from the groups consisting of monomeric and polymeric forms of 1,2-alkyldiamines, and monomeric and polymeric forms of 1,3-alkyldiamines, and combinations thereof, with the proviso that the first organic amine is present in said antimicrobial composition in an amount sufficient to insure that said amine component is soluble in said antimicrobial composition;

wherein all weight percents are based on the total weight of said antimicrobial composition, and wherein said antimicrobial composition has an enhanced biocidal effect against free-living microorganisms or biofilms.

In yet another aspect, the present invention relates to a method for providing a stable, soluble antimicrobial concentrate comprising from about 0.5% to about 20% of pyrithione, and a zinc source in an amount for from about 0.01% to about 5%. The method comprises incorporating into said concentrate a stabilizing effective amount of at least one organic amine component selected from the group consisting of a first organic amine selected from the group consisting of 1,2-alkanolamines, and 1,3-alkanolamines, and combinations thereof, alone or in combination with a second organic amine selected from the group consisting of monomeric and polymeric forms of 1,2-alkyldiamines, and monomeric and polymeric forms of 1,3-alkyldiamines, and combinations thereof, with the proviso that the first organic amine is present in said antimicrobial composition in an amount sufficient to insure that said amine component is soluble in said antimicrobial composition. Preferably, the stabilizing effective amount of said organic amine is from 30% to about 80% based upon the total weight of said organic amine plus said zinc source plus said pyrithione.

In still another aspect, the present invention relates to a method of inhibiting the growth of free-living microorganisms or biofilm in a metalworking fluid, comprising the steps of:

(A) incorporating the above antimicrobial composition concentrate into a metalworking fluid "masterbatch" concentrate comprising:
  (a) from about 0.05 to about 5% pyrithione or a pyrithione complex;
  (b) from about 0.005 to about 1% of a zinc source selected from the group consisting of zinc salts, zinc oxides, zinc borates, zinc hydroxides, zinc sulfates, zinc chlorides, zinc alloys, zinc complexes, and combinations thereof;
  (c) from about 0.5 to about 40% of an organic amine or combination of organic amines where the first essential organic amine is selected from the group consisting of 1,2-alkanolamines, and 1,3-alkanolamines, and combinations thereof, alone or in combination with a second organic amine selected from the group consisting of monomeric and polymeric forms of 1,2-alkyldiamines, and monomeric and polymeric forms of 1,3-alkyldiamines, and combinations thereof, (B) diluting said "masterbatch" concentrate to provide an antimicrobially effective metalworking fluid, and (C) contacting said free-living microorganisms or biofilm with the antimicrobially effective metalworking fluid, said antimicrobially effective metalworking fluid, wherein said antimicrobial composition has an enhanced biocidal effect against free-living microorganisms or biofilms in a metalworking fluid.

These and other aspects of the present invention will become apparent upon reading the following detailed description of the invention.

DETAILED DESCRIPTION OF THE INVENTION

It now has been surprisingly found, in accordance with the present invention, that a solution is provided to the problem of providing a soluble, stable and concentrated biocidal composition that possesses enhanced biocidal efficacy relative to pyrithione or its derivatives alone and which can be usefully, efficiently, and cost effectively delivered to applications. The present inventors have solved this problem by developing an antimicrobial composition concentrate exhibiting solubility of its components, as well as stability against unwanted precipitation of the concentrate's components. This soluble, stable antimicrobial composition concentrate comprises pyrithione or a pyrithione complex in combination with a zinc source, for example, a zinc salt, and certain 1,2-alkanolamines, and 1,3-alkanolamines, and combinations thereof, alone or in combination with a second organic amine selected from the group consisting of monomeric and polymeric forms of 1,2-alkyldiamines, and monomeric and polymeric forms of 1,3-alkyldiamines, and combinations thereof. Particularly preferred organic amines are monoethanolamine, 1-amino-2-propanol, 3-amino-1-propanol, and combinations thereof. Advantageously, the zinc source employed in the present invention is selected from the group consisting of zinc salts, zinc oxides, zinc borates, zinc hydroxides, zinc sulfates, zinc chlorides, zinc alloys, zinc complexes, and combinations thereof.

The composition concentrate of the present invention is suitably diluted to provide a so-called "masterbatch" for a functional fluid, such as a metalworking fluid concentrate or other coating composition, such as a paint. The masterbatch suitably contains, for example, from 0.05% to 5% by weight of pyrithione, and the other components of the composition concentrate are proportionately diluted in preparing the masterbatch.

In the antimicrobial composition concentrate, the masterbatch, and the final "working" functional fluid, the antimicrobial combination of the present invention exhibits both "in-can" preservation and an enhanced biocidal effect, relative to pyrithione alone, and relative to pyrithione and zinc alone, against a wide range microorganisms in both the free-living and biofilm state. This antimicrobial performance is greater than might be expected based upon the additive effect of the individual components of this composition. The enhanced biocidal effectiveness associated with the composition of the present invention permits the use of smaller amounts of the pyrithione component of the present composition, as compared to the conventionally employed amounts of pyrithione-based biocides.

As defined herein, the term "enhanced biocidal effect" refers to an interaction between the pyrithione or pyrithione salt component, the water-soluble zinc component, and the organic amine component that results in the biocidal effect of the composition being greater than any of the components taken individually. Thus, the antimicrobial results of the composition exceed the expected biocidal effect of the combination based upon the performance of the individual components.

The present invention also permits manufacture of a concentrated, stable and soluble biocidal composition of pyrithione or pyrithione salt component, and a zinc component. Such a composition allows the simultaneous delivery of high concentrations of solubilized pyrithione and zinc components, and the resultant enhanced biocidal effects, efficiently to an application.

In another advantageous aspect, the invention permits the use of pyrithione in applications containing iron. The presence of iron in applications commonly results in reduced efficacy of pyrithiones, and an accompanying blue discoloration of the application due to the formation of iron pyrithione. Compared to pyrithione, the present invention displays a higher efficacy and a reduced propensity for discoloration when utilized in the presence of iron.

The following discussion elaborates on several particular features of biofilms. As defined herein, the term "biofilm" refers to any aggregate of cells anchored to one another, or to surfaces, by extracellular slime. While most unicellular organisms produce a protective coating of slime, cells aggregated into biofilms are physically different from free-living cells and produce much more extracellular slime than free-living cells. The slime structures which make up part of the biofilm are quite complex both biologically and architecturally. They are composed of discreet microbial aggregates (microcolonies) separated by water channels which can form large tower-shaped or mushroom-shaped structures. As biofilms develop, free-living cell detach from the biofilm and migrate through the environment in search of new areas to colonize and form new biofilm. In metalworking fluids, a buildup of biofilms can cause many problems, including fluid deterioration/degradation, foul odors, corrosion, clogging of filters, transfer lines, nozzles, and crevices, fouling of machine surfaces, machine down-time, shorter tool life, fouling and damage of the workpiece, and the like. As mentioned above, biofilms can also enhance the rate of degradation of other fluids such as paints or other surface coatings. Medical equipment, such as cardiac implants, catheters, dialysis machines, dental waterlines, and the like, may also become contaminated by biofilms and spread infection.

Biofilms possess extensive physical and chemical heterogeneity which is not found in the free-living cells residing in bulk fluid. Because biofilm cells are in intimate contact with one another in the biofilm, ecological interaction between the individual organisms can become complex and extensive. Due to the high degree of complexity and heterogeneity that is present in a biofilm, biofilm cells possess dramatically different metabolic parameters as compared to free-living cells (e.g., metabolic rate, growth rate, preference for specific nutrients, etc.). In addition, cells found in biofilms generally display a greater diversity of species and organism types as compared to free-living cells found in bulk fluid. Each of the components of the compositions of the present invention is discussed in more detail below.

Pyrithione in its acid form, or a pyrithione complex may be used in the composition of the present invention. As defined herein, the term "pyrithione complex" refers to combinations of one or more pyrithione molecules and one or more metal atoms, such as pyrithione salts and adducts of pyrithione (e.g., 2,2'-dithiopyridine-1,1'-dioxide in combination with a metal ion such as magnesium). Examples of pyrithione salts that are useful in the present composition include sodium pyrithione, bismuth pyrithione, potassium pyrithione, lithium pyrithione, ammonium pyrithione, zinc pyrithione, copper pyrithione, calcium pyrithione, magnesium pyrithione, strontium pyrithione, silver pyrithione, gold pyrithione, manganese pyrithione, and combinations thereof. Also useful is the organic amine salt of pyrithione, as well as the magnesium disulfide salt. The two most preferred salts of pyrithione useful in the present invention are the sodium salt (i.e., sodium pyrithione) and zinc pyrithione. Sodium pyrithione is a well-known commercial product that is commonly made by reacting 2-chloropyridine-N-oxide with NaSH and NaOH, as illustrated in the disclosure of U.S. Pat. No. 3,159,640. Zinc pyrithione may be made by reacting 1-hydroxy-2-pyridinethione (i.e., pyrithione acid) or a soluble salt thereof with a zinc salt (e.g., zinc sulfate) to form a zinc pyrithione precipitate, as illustrated in U.S. Pat. No. 2,809,971.

In the composition concentrates of the present invention, the pyrithione or pyrithione complex is suitably employed in an amount in the range of from about 0.05 to about 20 wt. %, preferably from about 0.5 to about 15 wt. %, more preferably from about 1 to about 10 wt. %. From this composition concentrate, a "masterbatch" is suitably prepared with the pyrithione or pyrithione complex present in an amount in the range of from about 0.05% to about 5 wt. %, more preferably from about 0.01% to about 2.5 wt. %, all based on the total weight of the composition.

Zinc sources useful in the composition of the present invention include, for example, zinc alloys, zinc salts, zinc oxides, zinc hydroxides, zinc sulfates, zinc chlorides, zinc borates, and combinations thereof.

Examples of zinc salts that may be used in the composition of the present invention include zinc acetate, zinc oxide, zinc borate, zinc carbonate, zinc hydroxide, zinc chloride, zinc sulfate, zinc citrate, zinc fluoride, zinc iodide, zinc lactate, zinc oleate, zinc oxalate, zinc phosphate, zinc propionate, zinc salicylate, zinc selenate, zinc silicate, zinc stearate, zinc sulfide, zinc tannate, zinc tartrate, zinc valerate, and the like. Combinations of zinc salts may also be used in the composition of the invention.

In the composition concentrates of the present invention, the zinc source is generally present in a range of from about 0.01 wt % to about 5 wt %, preferably from about 0.05 wt % to about 3 wt. %, based upon the weight of the concentrate. This enables the final "working" functional fluid to contain an amount of the zinc source within the range of from 0.005 to 1 wt. %, advantageously from 0.01 to 0.1 wt. %, all based on the total weight of the working fluid.

Desirably, the organic amine component comprises one or more 1,2 and 1,3 alkanolamines encompassed by the formula:

$$R^1NH-(CHR^2)_n-CHR^3-OH \qquad \text{(Formula 1)}$$

wherein n=1 or 2 and $R^1$, $R^2$, and $R^3$ are hydrogens or lower alkyl groups having a total number of carbons less than or equal to 4. Most preferred are 1,2-alkanolamines and 1,3-alkanolamines wherein:

| $R^1$ | $R^2$ | $R^3$ |
|---|---|---|
| H | H | H |
| $CH_3$ | H | H |
| $C_2H_5$ | H | H |
| n-$C_3H_7$ | H | H |
| i-$C_3H_7$ | H | H |
| H | $CH_3$ | H |
| H | H | $CH_3$ |

Also useful as the amine component in the present invention is any soluble combination of one or more alkanolamines encompassed by Formula 1 with one or more alkanolamines encompassed by the formula:

$$NR^1R^2R^3 \quad \text{(Formula 2)}$$

wherein
1) $R^1=R^2=R^3=HO-CH_2-CH_2-$;
2) $R^1=R^2=R^3=HO-CH(CH_3)-CH_2-$;
3) $R^1=R^2=CH_3-$ and $R^3=HO-CH_2-CH_2-$;
4) $R^1=R^2=CH_3CH_2-$ and $R^3=HO-CH_2-CH_2-$;
5) $R^1=R=CH_3CH_2CH_2-$ and $R=HO-CH_2-CH_2-$;
6) $R^1=R^2=CH_3CH_2CH_2CH_2-$ and $R^3=HO-CH_2-CH_2-$;
7) $R^1=R^2=CH_3-$ and $R^3=HO-CH(CH_3)-CH_2-$;
8) $R^1=R=CH_3CH_2-$ and $R^3=HO-CH(CH_3)-CH_2-$;
9) $R^1=R=CH_3CH_2CH_2-$ and $R=HO-CH(CH_3)-CH_2-$;
10) $R^1=R^2=CH_3CH_2CH_2CH_2-$ and $R^3=HO-CH(CH_3)-CH_2-$;
11) $R^1=R^2=CH_3-$ and $R^3=HO-CH_2-CH_2-CH_2-$,
12) $R^1=R^2-CH_3CH$ and $R^3=HO-CH_2-CH_2-CH_2-$;
13) $R^1=R\ CH_3CH_2CH_2-$ and $R^3=HO-CH_2-CH_2-CH_2-$;
14) $R^1=R^2=CH_3CH_2CH_2CH_2-$ and $R^3=HO-CH_2-CH_2-CH_2-$;
15) $R^1=CH_3-$ and $R^2=R^3=HO-CH_2-CH_2-$;
16) $R^1=CH_3CH_2-$ and $R^2=R^3=HO-CH_2-CH_2-$;
17) $R^1=CH_3CH_2CH_2-$ and $R^2=R^3=HO-CH_2-CH_2-$;
18) $R^1=CH_3CH_2CH_2CH_2-$ and $R^2=R^3=HO-CH_2-CH_2-$;
19) $R^1=CH_3-$ and $R^2=R^3=HO-CH(CH_3)-CH_2-$;
20) $R^1=CH_3CH_2-$ and $R^2=R^3=HO-CH(CH_3)-CH_2-$;
21) $R^1=CH_3CH_2CH_2-$ and $R^2=R^3=HO-CH(CH_3)-CH_2-$;
21) $R^1=CH_3CH_2CH_2CH_2-$ and $R^2=R^3=HO-CH(CH_3)-CH_2-$;
23) $R^1=CH_3-$ and $R^2=R^3=HO-CH_2-CH_2-$;
24) $R^1=CH_3CH_2-$ and $R^2=R^3=HO-CH_2-CH_2-CH_2-$;
25) $R^1=CH_3CH_2CH_2-$ and $R^2=R^3=HO-CH_2-CH_2-$;
26) $R^1=CH_3CH_2CH_2-$ and $R^2=R^3=HO-CH_2-CH_2-$;
27) $R^1=H-$ and $R^2=R^3=HO-CH_2-CH_2-$;
28) $R^1=H-$ and $R^2=R^3=HO-CH(CH_3)-CH_2-$;
29) $R^1=H-$ and $R^2=R^3=HO-CH_2-CH_2-$;
30) $R^1=R^2=H$ and $R^3=HO-CH_2-C(CH_3)_2-$;
31) $R^1=H$ and $R^2=CH_3-$ and $R^3=HO-CH_2-C(CH_3)_2-$;
32) $R^1=R^2=CH_3-$ and $R^3=HO-CH_2-C(CH_3)_2-$;
33) $R^1=R^2=H$ and $R^3=(HOCH_2)_2C(CH_2CH_3)$
34) $R^1=R^2=H$ and $R^3=HO-CH_2-CH_2-O-CH_2-CH_2-$;
35) $R^1=H$ and $R^2=CH_3-$ and $R^3=HO-CH_2-CH_2-O-CH_2-CH_2-$;
36) $R^1=R^2=CH_3-$ and $R^3=HO-CH_2-CH_2-O-CH_2-CH_2-$;

Also useful as the amine component in the present invention is any soluble combination of one or more amines encompassed by Formula 1 and one or more amines selected from the group consisting of monomers and polymers of alkyl diamines of the formula:

$$R^1R^2N-[(CH_2)_n-CH_2-NH-]_m-H \quad \text{(Formula 3)}$$

where: n is 1 or 2, and m is about 1 to about 2000, and $R^1$ and $R^2$ are hydrogens or lower alkyl groups having a total number of carbons less than or equal to 4. Examples of amine compounds within the scope of Formula 3 are those having the following substitutents: 1) $R^1=R^2=CH_3-$ and n=2 and m=2; 2) $R^1=R^2=CH_3CH_2$ and n=2 and m=1; 3) $R^1=R^2=H$ and n=1 and m=1; 4) $R^1H$ and n=1 and m=2; 5) $R^1=R^2=H$ and n=1 and m=3.

Within the above-recited Formulas 1, 2 and 3, the following amines are particularly preferred:
(Formula 1)
Ethanolamine
1-Amino-2-Propanol
3-Amino-1-Propanol
2-(methylamino)ethanol
2-(ethylamino)ethanol
2(propylamino)ethanol
2(isopropylamino)ethanol
(Formula 2)
Diethanolamine
Triethanolamine
Diisopropanolamine
Triisopropanolamine
Mixed Isopropanolamines (mono-, di-, and triisopropanolamines)
2-Amino-2-methyl-1-propanol (also called AMP)
2-Amino-2-ethyl-1,3-propanediol (also called AEPD)
2(2-Aminoethoxy)ethanol (also called diglycol amine)
N-Methyldiethanolamine
N,N-Dimethylethanolamine
N,N-Diethylethanolamine
N,N-Dibutylaminoethanol
N,N Dimethylamino-2-propanol
(Formula 3)
1,3-Diaminopropane
Diethylenetriamine
Triethylenetetraamine
Polyethylene imine
Diethylamino propylamine
Dimethylaminopropylamine The amount of organic amine suitably employed in the composition concentrates of the present invention suitably ranges from about 30 to about 80 wt %, preferably from about 40 to about 70 wt %, based upon the total weight of the concentrate. Upon dilution in the "masterbatch" or the "working" functional fluid, the organic amine amount is suitably from about 0.5 to 40 wt %, based upon the weight of the fluid.

A solvent or combination of solvents may be included in the antimicrobial composition of the invention. Suitable solvents include aqueous media such as water, or water in combination with one or more water-miscible organic solvent(s). Useful organic solvents include alcohols, such as methanol, ethanol, ethers, esters, glycols, and the like.

The composition of the invention may also include formaldehyde as an additional biocide. In the present invention, formaldehyde may be added directly, or in the form of a formaldehyde-releasing agent or donor such as, but not limited to, cis 1-(3-chloroallyl)-3,5,7-triaza-1-azoniaadamantane chloride, hexahydro-1,3,5-tris(2-hydroxyethyl)-s-triazine, 4,4-dimethyloxazolidine, 5-hydroxymethoxymethyl-1-1 aza-3,7-dioxabicyclo-octane, dimethyloldimethyldantoin, N,N"-methylene bis [N'-[hydroxymethyl)-2,5-dioxo-4-imidazolidinyl]urea], N-(hydroxymethyl)-N-(1,3-dihydroxymethyl-2,5-dioxo-4-imidazolidinyl)-N'-(hydroxymethyl) urea, and combinations thereof. One useful formaldehyde-releasing agent is TRIADINE 10 (a combination of hexahydro-1,3,5-tris(2-hydroxyethyl)-s-triazine and omadine salts sold by Arch Chemicals, Inc. Norwalk, Conn.). In the composition concentrates of the present invention, the formaldehyde is suitably employed in an amount in the range of from about 0.1 to about 30 wt. %, preferably from about 0.5% to about 15 wt %, based on the total weight of the composition.

As is known in the art, in the case of many formaldehyde-releasing agents, generally only a fraction of the material is released to form formaldehyde. For example, about 31% of hexahydro-1,3,5-tris(2-hydroxyethyl)-s-triazine undergoes formaldehyde release. In such cases, the appropriate conversion factor must be taken into account in order to provide the above ranges of formaldehyde in the composition of the invention. In an illustrative example, 500 ppm of hexahydro-1,3,5-tris(2-hydroxyethyl)-s-triazine results in about 160 ppm of formaldehyde being released. Similarly, 1500 ppm of hexahydro-1,3,5-tris(2-hydroxyethyl)-s-triazine results in about 480 ppm of formaldehyde being released.

Advantageously, the composition of the invention can be made by first mixing together one or more selected zinc sources and one or more organic 1,2- or 1,3-alkanolamines and optionally monomers and polymers of 1,2- or 1,3-alkyldiamines in an appropriate solvent or carrier, and then adding the pyrithione or pyrithione complex. Alternatively, the composition of the invention may be made by adding the individual components separately to a solvent or functional blend or fluid being treated to impart antimicrobial protection.

The biocidal composition of the invention is useful as an algaecide, bactericide, and/or fungicide, and is particularly useful in inhibiting the growth of microorganisms such as gram positive bacteria, gram negative bacteria, fungi (e.g. yeast, mold, mildew), algae and protozoa. The composition is particularly effective against *Pseudomonas aeruginosa, Aspergillus niger, Fusarium, Cephalosporium, Pseudomonas fluorescens, Pseudomonas rubescens, Pseudomonas stutzeri, Pseudomonas olevorans, Alcaligenes faecalis, Escherichia coli, Citrobacter freundii*, and the like. The biocidal composition of the invention is a useful additive in industrial fluids (e.g., metalworking fluids), paints, coatings, adhesives, wet-state preservatives, hard surface cleaners, fabric care compositions, wood products, plastic products, medical products, fibers, or any other application where microorganism growth, and particularly biofilm growth, must be stopped or slowed.

One significant use application for the antimicrobial compositions of the present invention is in functional fluids, such as metalworking fluids, cutting fluids and the like. Metalworking fluids are typically supplied as a "masterbatch" concentrate containing the antimicrobial composition and the other components of the formulation. In the concentrate, a sufficient amount of the antimicrobial composition is provided such that the diluted "working" fluid will contain a biocidally effective amount thereof. In order to satisfy this requirement, antimicrobials are typically incorporated into the concentrate of metalworking fluid in an amount of from about 10 to 100 times the concentrations required in diluted "working" fluid. Typical concentrations of pyrithione in metalworking concentrates range from about 0.05 to 1.0% pyrithione. At these concentrations of pyrithione, small amounts of zinc will result in the formation of a precipitate, which is unacceptable for use in a metalworking fluid concentrate.

The present biocidal composition permits the addition of combinations of pyrithione and zinc at concentrations that are sufficient for use in a metalworking fluid concentrate, yet do not form precipitates when formulated as concentrated biocidal compositions or in the metalworking fluid concentrates. In this manner, the enhanced biocidal effects imparted by the present biocidal composition can be efficiently provided for use in metalworking fluid concentrates in a concentrated, soluble form. Particularly useful levels of the prototype biocide blend in metalworking concentrates would be about 1 to 4%, and about 0.05 to 0.2% ppm in diluted "working" metalworking fluid. Advantageously, the diluted metalworking fluid resulting from these concentrates will provide concentrations of 10 to 500 ppm active sodium pyrithione, 1 to 50 ppm bivalent zinc, and 150 to 1500 ppm organic 1,2- and/or 1,3-alkanolamines and optionally monomers and polymers of alkyldiamines; more preferably from 25 to 250 ppm active sodium pyrithione, 5 to 25 ppm bivalent zinc, and 150 to 1200 ppm organic 1,2- and/or 1,3-alkanolamines and optionally monomers and polymers of alkyldiamines. A particularly useful ratio of components in the final "working" metalworking fluid is about 100 ppm. active sodium pyrithione, about 10 ppm zinc, and about 600 ppm organic 1,2- and/or 1,3-alkanolamines and optionally monomers and polymers of alkyldiamines.

The antimicrobial compositions of the present invention are also useful in coating compositions, such as paints, adhesives, caulks, sealants, elastomers, and other coating compositions, including water-based liquid cleaning compositions, such as liquid detergent compositions. Suitable paints include indoor and outdoor household paints, industrial and commercial paints. Particularly advantageous results are obtained when the antimicrobial compositions of the present invention are utilized, preferably in a total amount of between about 0.01% and about 10% by weight based upon the weight of the coating composition, as in-can "wet state" preservatives during storage and prior to the use of the coating composition.

The coating composition containing the antimicrobial combination of the present invention may be used in many end-use applications, such as, for example, adhesives, paints, coatings, sealants, wood and wood composites, wet state preservative compositions, personal care products, masonry and stone treatment compositions, leather care compositions, hard surface cleaners and disinfectants, textile and fabric care compositions, as well as in plastics and medical products applications. Illustratively, the antimicrobial combination is suitably incorporated into a functional fluid containing a component that is effective in treating a substrate, such as wood and wood composites, masonry and stone, leather, hard surfaces, textiles, fabrics, plastics, medical products, and combinations thereof.

The compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The present invention permits the use of reduced amounts of the pyrithione primary biocide, in conjunction with a zinc salt co-biocide that is less expensive than the primary biocide, thereby providing an antimicrobial composition that is inexpensive to produce and that possesses the above-mentioned characteristic of enhanced antimicrobial effectiveness against a variety of microorganisms. In addition, it is believed that the amine component of the composition of the invention provides significant solubility to the composition, as well as enhanced stability against the formation of precipitates, and allows the composition to remain commercially active for extended periods. Additionally, the present invention permits delivery of the enhanced biocidal composition of the pyrithione biocide, the zinc salt and the 1,2- and 1,3-alkanolamines alone or in combination with monomers and polymers of alkyldiamines in applications as a concentrated, soluble, and stable composition.

The following examples are intended to illustrate, but in no way limit the scope of the present invention. All parts and percentages are by weight and all temperatures are in degrees Celsius unless explicitly stated otherwise.

EXAMPLES

Examples 1-40

Efficacy of Mixtures of Sodium Pyrithione, $ZnCl_2$, and Amines Against Microorganisms in Metalworking Fluids Autoclaved 250 ml Erylenmeyer flasks with cheesecloth stoppers were arranged and into each flask was added 100 ml of one of the following diluted (1:20) metalworking fluid solutions: (1) soluble oil, (2) semi-synthetic fluid, or (3) synthetic fluid. Each of these fluids was designed to mimic commercially available soluble, semisynthetic and synthetic oils available from manufacturers.

The soluble oil was made from the following ingredients:

| | |
|---|---|
| 100 SUS naphthenic petroleum base stock | 82.5% |
| 62% active sodium sulfonate | 11.0% |
| oleic acid | 1.5% |
| triethanolamine (TEA) | 1.0% |
| methyl tallowate | 3.0% |
| glycol ether | 1.0% |

The Semi-Synthetic fluid was made from the following ingredients:

| | |
|---|---|
| 100 SUS naphthenic petroleum base stock | 5.0% |
| 62% sodium sulfonate | 10.0% |
| TEA | 15.0% |
| Oleic acid | 15.0% |
| carboxylic acid type corrosion inhibitor | 10.0% |
| Water | 45.0% |

The Synthetic Concentrate fluid was made from the following ingredients:

| | |
|---|---|
| Water | 63.0% |
| Polyalkylene glycol (water soluble type) | 7.0% |
| Heptanoic acid | 1.0% |
| TEA | 15.0% |
| carboxylic acid type corrosion inhibitor | 14.0% |

In addition to untreated controls, flasks containing 100 PPM sodium pyrithione (NaPT) alone, 21 PPM $ZnCl_2$ alone, and 600 PPM of an amine alone (either monethanolamine, 1-amino-2-propanol, or 3-amino-1-propanol) were prepared for each metalworking fluid type. Also, flasks were set up for testing mixtures of 100 PPM NaPT and 21 PPM $ZnCl_2$, and mixtures of 21 PPM $ZnCl_2$ and 600 PPM of one of the above three amine compounds. For each fluid type, three treatment flasks were set up and treated with final concentrations of 1000 PPM of mixtures A, B, or C composed of NaPT, $ZnCl_2$, and one of the amines. Mixture A consisted of 10% NaPT, 1.8% $ZnCl_2$ and 60.5% monoethanolamine. Mixture B consisted of 10% NaPT, 1.8% $ZnCl_2$ and 60.5% 1-amino-2-propanol. Mixture C consisted of 10% NaPT, 1.8% $ZnCl_2$ and 60.5% 3-amino-1-propanol. All concentrations displayed above for controls are the final concentrations of the compounds in the test flasks. Final concentrations of the mixing components in the treatment test flasks were 100 PPM NaPT, 18 PPM $ZnCl_2$ and 605 PPM amine.

The pH of each flask was determined. The addition of the amines to soluble oil flasks raised the pH of the fluid to about 9.9. For any such flask, the pH was adjusted to the pH of the untreated control by the addition of HCl. This was done to eliminate or minimize any biocidal effects against the test organism due to pH. In semi-synthetic or synthetic fluids, amines raised the pH no more than 0.3 over the untreated controls. The pH of the soluble oil, semi-synthetic and synthetic flasks were 8.5 to 8.7, 8.2 to 8.5, and 8.1 to 8.5, respectively. To each flask, bacteria were added to final concentration of $10^7$ bacteria/ml. The bacterial innoculum consisted of an equal number of cells from *Pseudomonas aeruginosa* 9027, *Escherichia coli* 8739, *Pseudomonas fluorescens* 12201, *Pseudomonas rubescens* 12202, and *Pseudomonas putida*. Fungal spores were added to each flask to final concentration of $10^5$ spores/ml. Fungal additions consisted of an equal number of spores from *Fusarium* sp. and *Cephalosporium* sp. metalworking fluid field isolates.

Flasks were incubated at room temperature (23° C.±2° C.) on a shaker at 130 rpms. Fluid samples were obtained from flasks after one and four days of incubation. Samples were serially diluted (1:10) in sterile, de-ionized water and spread plated for bacterial and fungal viable counts. Plates were incubated at 28° C. for two to three days and then scored for colony forming units. Experimental results are displayed in Table 1.

TABLE 1

Efficacy of mixture of Sodium pyrithione, $ZnCl_2$ and amines against bacteria and fungi.

| | | Bacteria/ml | | Fungi/ml | |
|---|---|---|---|---|---|
| Example | Treatment | Day 1 | Day 4 | Day 1 | Day 4 |
| 1 | Soluble Oil | | | | |
| 2 | Untreated | $6.6 \times 10^6$ | $2.9 \times 10^6$ | $6.3 \times 10^4$ | $3.9 \times 10^4$ |
| 3 | 100 PPM NaPT | $4.3 \times 10^6$ | $6.0 \times 10^6$ | $5.7 \times 10^4$ | $4.6 \times 10^4$ |
| 4 | 21 PPM $ZnCl_2$ | $1.4 \times 10^7$ | $2.9 \times 10^6$ | $7.7 \times 10^4$ | $4.3 \times 10^4$ |
| 5 | 100 PPM NaPT + 21 PPM $ZnCl_2$ | $2.9 \times 10^6$ | $1.9 \times 10^6$ | $4.5 \times 10^4$ | $2.0 \times 10^4$ |
| 6 | 600 PPM monoethanolamine | $6.0 \times 10^5$ | $6.0 \times 10^5$ | $2.9 \times 10^4$ | $1.0 \times 10^4$ |
| 7 | 600 PPM 1-amino-2-propanol | $2.2 \times 10^6$ | $1.3 \times 10^6$ | $4.6 \times 10^4$ | $2.5 \times 10^4$ |

TABLE 1-continued

Efficacy of mixture of Sodium pyrithione, ZnCl$_2$ and amines against bacteria and fungi.

| Example | Treatment | Bacteria/ml Day 1 | Bacteria/ml Day 4 | Fungi/ml Day 1 | Fungi/ml Day 4 |
|---|---|---|---|---|---|
| 8 | 600 PPM 3-amino-1-propanol | $1.0 \times 10^6$ | $2.0 \times 10^6$ | $5.4 \times 10^4$ | $1.4 \times 10^4$ |
| 9 | 600 PPM MEA + 21 PPM ZnCl$_2$ | $1.3 \times 10^6$ | $4.3 \times 10^6$ | $5.9 \times 10^4$ | $1.0 \times 10^4$ |
| 10 | 600 PPM 1A2P + 21 PPM ZnCl$_2$ | $1.4 \times 10^6$ | $8.0 \times 10^5$ | $6.9 \times 10^4$ | $1.8 \times 10^4$ |
| 11 | 600 PPM 3A1P + 21 PPM ZnCl$_2$ | $2.5 \times 10^6$ | $6.0 \times 10^5$ | $5.2 \times 10^4$ | $2.9 \times 10^4$ |
| 12 | 1000 PPM Mixture A | $9.1 \times 10^4$ | $2.0 \times 10^3$ | $3.5 \times 10^4$ | 10 |
| 13 | 1000 PPM Mixture B | $5.9 \times 10^4$ | $1.5 \times 10^4$ | $1.5 \times 10^4$ | 0 |
| 14 | 1000 PPM Mixture C | $7.5 \times 10^4$ | $1.6 \times 10^4$ | $3.7 \times 10^4$ | 50 |
| | Semi-Synthetic Fluid | | | | |
| 15 | Untreated | $4.0 \times 10^5$ | $8.0 \times 10^5$ | $5.0 \times 10^4$ | $1.4 \times 10^4$ |
| 16 | 100 PPM NaPT | $4.0 \times 10^5$ | $3.0 \times 10^5$ | $5.1 \times 10^4$ | $2.1 \times 10^4$ |
| 17 | 21 PPM ZnCl$_2$ | $3.0 \times 10^6$ | $1.1 \times 10^6$ | $5.9 \times 10^4$ | $3.2 \times 10^4$ |
| 18 | 100 PPM NaPT + 21 PPM ZnCl$_2$ | 0 | 0 | $1.8 \times 10^4$ | $1.0 \times 10^4$ |
| 19 | 600 PPM MEA | $6.8 \times 10^4$ | 30 | $4.3 \times 10^4$ | $7.0 \times 10^4$ |
| 20 | 600 PPM 1A2P | $7.2 \times 10^4$ | $3.0 \times 10^5$ | $4.7 \times 10^4$ | $5.0 \times 10^4$ |
| 21 | 600 PPM 3A1P | $5.2 \times 10^4$ | $6.1 \times 10^4$ | $5.7 \times 10^4$ | $2.4 \times 10^4$ |
| 22 | 600 PPM MEA + 21 PPM ZnCl$_2$ | $9.5 \times 10^4$ | 30 | $5.5 \times 10^4$ | $1.4 \times 10^4$ |
| 23 | 600 PPM 1A2P + 21 PPM ZnCl$_2$ | $4.0 \times 10^5$ | $4.0 \times 10^5$ | $4.0 \times 10^4$ | $1.4 \times 10^4$ |
| 24 | 600 PPM 3A1P + 21 PPM ZnCl$_2$ | $5.0 \times 10^5$ | $1.5 \times 10^4$ | $4.1 \times 10^4$ | $1.4 \times 10^4$ |
| 25 | 1000 PPM Mixture A | 0 | 0 | $3.1 \times 10^4$ | 10 |
| 26 | 1000 PPM Mixture B | 0 | 0 | $2.3 \times 10^4$ | 0 |
| 27 | 1000 PPM Mixture C | 0 | 0 | $2.8 \times 10^4$ | 10 |
| | Synthetic Fluid | | | | |
| 28 | Untreated | $1.0 \times 10^7$ | $2.7 \times 10^7$ | $2.5 \times 10^4$ | $1.0 \times 10^4$ |
| 29 | 100 PPM NaPT | $5.2 \times 10^6$ | $3.7 \times 10^7$ | $7.0 \times 10^4$ | $3.6 \times 10^4$ |
| 30 | 21 PPM ZnCl$_2$ | $9.0 \times 10^4$ | 0 | $5.2 \times 10^4$ | $3.1 \times 10^4$ |
| 31 | 100 PPM NaPT + 21 PPM ZnCl$_2$ | $2.0 \times 10^6$ | $2.0 \times 10^5$ | $5.5 \times 10^4$ | $2.4 \times 10^4$ |
| 32 | 600 PPM MEA | $1.5 \times 10^5$ | $3.0 \times 10^3$ | $4.7 \times 10^4$ | $3.6 \times 10^4$ |
| 33 | 600 PPM 1A2P | $2.2 \times 10^6$ | $1.8 \times 10^4$ | $5.5 \times 10^4$ | $3.6 \times 10^4$ |
| 34 | 600 PPM 3A1P | $1.5 \times 10^5$ | 800 | $3.8 \times 10^4$ | $5.5 \times 10^4$ |
| 35 | 600 PPM MEA + 21 PPM ZnCl$_2$ | $2.2 \times 10^4$ | 0 | $4.6 \times 10^4$ | $1.8 \times 10^4$ |
| 36 | 600 PPM 1A2P + 21 PPM ZnCl$_2$ | $1.0 \times 10^3$ | 0 | $3.6 \times 10^4$ | $2.7 \times 10^4$ |
| 37 | 600 PPM 3A1P + 21 PPM ZnCl$_2$ | $1.1 \times 10^6$ | 0 | $6.6 \times 10^4$ | $8.5 \times 10^4$ |
| 38 | 1000 PPM Mixture A | $1.9 \times 10^6$ | $2.0 \times 10^3$ | $2.9 \times 10^4$ | $2.0 \times 10^4$ |
| 39 | 1000 PPM Mixture B | $3.3 \times 10^6$ | $7.0 \times 10^5$ | $5.0 \times 10^4$ | $3.3 \times 10^4$ |
| 40 | 1000 PPM Mixture C | $2.9 \times 10^6$ | $9.0 \times 10^4$ | $4.5 \times 10^4$ | $1.8 \times 10^4$ |

MEA, monoethanolamine;
1A2P, 1-amino-2-propanol;
3A1P, 3-amino-1-propanol.
Mixture A, 10% NaPT, 1.8% ZnCl$_2$, 60.5% MEA;
Mixture B, 10% NaPT, 1.8% ZnCl$_2$, 60.5% 1A2P;
Mixture C, 10% NaPT, 1.8% ZnCl$_2$, 60.5% 3A1P.
Treatment concentrations shown are final concentrations in diluted (1:20) metalworking fluid.

As shown in Table 1, treatments with final concentrations of 1000 PPM of mixture A (10% NaPT, 1.8% ZnCl$_2$ and 60.5% monoethanolamine) mixture B (10% NaPT, 1.8% ZnCl$_2$, and 60.5% 1-amino-2-propanol), or mixture C (10% NaPT, 1.8% ZnCl$_2$, and 60.5% 3-amino-1-propanol) were very effective against fungi in soluble oil and semi-synthetic fluids. No fungi were detected in flasks treated with these mixtures after four days. Control treatments demonstrated little difference of fungal counts in the soluble oil and synthetic fluids compared to the untreated control. All three mixtures A, B, and C showed at least 100-fold fewer bacteria in soluble oils within four days compared to untreated and reduced counts to zero in the semi-synthetic fluid within one day. Relative to untreated controls, bacterial counts were not affected much by the control treatments in soluble oil and semi-synthetic fluids. Mixtures A and C reduced bacteria counts in the synthetic fluid by about at least 500-fold and 10-fold respectively. In the synthetic fluid, controls containing zinc alone were very effective against bacteria. None of the mixtures had much effect on fungi in the synthetic fluid.

Examples 41-51

Biocidal Efficacy of a Mixture of Sodium Pyrithione, ZnCl$_2$, and Amines Against Free-Living Microorganisms and Biofilm Associated Microorganisms in Metalworking Fluid Two five gallon glass aquarium tanks were disinfected with bleach and set up to simulate recirculating metalworking fluid systems. One aquarium pump was attached to each tank as a means to recirculate fluid through the tank. To provide sampling surfaces for biofilm growth, stainless steel washer coupons (1.2 cm$^2$ surface area) and polycarbonate disc coupons (3.8 cm$^2$ surface area) were attached to glass slide coupon holders with double stick carpet tape. Two steel and polycarbonate coupons were placed on each holder. 12.5 liters of dilute (1:20) semi-synthetic metalworking fluid was added to each tank.

Tank 1 served as an untreated control. Mixture D (16% NaPT, 2% ZnCl$_2$, 20% monoethanolamine, 20% 3-amino-1-propanol) was added to tank 2 to a final concentration of 1250 PPM which yielded final active concentrations of 200 PPM NaPT, 25 PPM ZnCl$_2$, 250 PPM monoethanolamine, and 250 PPM 3-amino-1-propanol in the 12.5 liters of diluted metalworking fluid. The pH of tank 1 and tank 2 was 7.8 and 8.3, respectively. pH of tank 1 was adjusted to 8.3 with HCl. To each tank, bacteria were added to a final concentration of 10$^6$ bacteria/ml. The bacterial innoculum consisted of an equal number of cells from *Pseudomonas aeruginosa* 9027, *Escherichia coli* 8739, *Pseudomonas fluorescens* 12201, *Pseudomonas rubescens* 12202, and *Pseudomonas putida*. Fungal spores were added to each flask to final concentration of 10$^4$ spores/ml. Fungal additions consisted of an equal number of spores from *Fusarium* sp. and *Cephalosporium* sp. metalworking fluid field isolates. Bacterial and fungal additions were repeated three times per week. Tanks were recirculated at room temperature (23° C.±2° C.).

Samples of the bulk metalworking fluid and biofilm were obtained after 19 days. For bulk fluid, samples were serially diluted (1:10) in sterile, de-ionized water and spread plated for bacterial and fungal viable counts on Tryptic Soy Agar plus 90 PPM cyclohexamide and Malt Agar plus 900 PPM streptomycin plus 550 PPM Penicillin G, respectively. For biofilm samples, coupon holders were removed from the bottom and sides of the tanks. Coupons were removed from the holders, dip rinsed in sterile water, and transferred to 25 mm×150 mm glass disposal culture tubes containing 10 ml of sterile, de-ionized water. Biofilms were liberated from the coupons and resuspended by vortexing tubes at maximum speed for 30 seconds. Resuspended biofilms were then serially diluted and plated for bacteria and fungal counts as described for bulk fluid samples. 0.5 ml of slime material from the sides of the tank at the fluid-air interface were sampled by a sterile, needleless syringe and resuspended in sterile, de-ionized water and by vortexing. Counts of bacterial and fungi in the slime samples were also determined as described previously for bulk fluid samples. Plates were incubated at 28° C. for two to three days and then scored for colony forming units (cfu). For biofilm samples, excepting the slime material, colony forming units per ml were converted to colony forming units per cm$^2$. Table 2 displays the results of this experiment.

TABLE 2

Biocidal Efficacy of a Mixture of Sodium pyrithione, ZnCl$_2$, Monoethanolamine, and 3-Amino-1-propanol.

| Example | Sample | Untreated Bacteria/ml | Untreated Fungi/ml | Treated by Mixture D Bacteria/ml | Treated by Mixture D Fungi/ml |
|---|---|---|---|---|---|
| | Bulk Fluid | | | | |
| 41 | 1 | $1.3 \times 10^7$ | $7.0 \times 10^3$ | $5.4 \times 10^4$ | $1.3 \times 10^3$ |
| 42 | 2 | $1.2 \times 10^7$ | $6.0 \times 10^3$ | $5.7 \times 10^4$ | $1.3 \times 10^3$ |
| | Biofilm tank floor Stainless Steel | | | | |
| 43 | 1 | $4.4 \times 10^6$ | $9.2 \times 10^4$ | $3.0 \times 10^2$ | $7.2 \times 10^3$ |
| 44 | 2 | $2.0 \times 10^6$ | $1.3 \times 10^5$ | $9.8 \times 10^2$ | $4.7 \times 10^2$ |
| | Polycarbonate | | | | |
| 45 | 1 | $5.6 \times 10^6$ | $1.5 \times 10^5$ | $2.8 \times 10^2$ | $7.5 \times 10^1$ |
| 46 | 2 | $2.4 \times 10^6$ | $1.3 \times 10^5$ | $7.6 \times 10^2$ | $8.5 \times 10^2$ |
| | Biofilm tank side Stainless Steel | | | | |
| 47 | 1 | $2.3 \times 10^6$ | $1.1 \times 10^4$ | $2.8 \times 10^3$ | $7.5 \times 10^1$ |
| 48 | 2 | $2.3 \times 10^6$ | $3.0 \times 10^4$ | $1.6 \times 10^3$ | $7.5 \times 10^1$ |
| | Polycarbonate | | | | |
| 49 | 1 | $2.8 \times 10^6$ | $2.0 \times 10^4$ | $2.6 \times 10^2$ | $2.0 \times 10^2$ |
| 50 | 2 | $2.0 \times 10^6$ | $1.6 \times 10^4$ | $8.0 \times 10^2$ | $6.0 \times 10^2$ |
| | Splash area slime tank side | | | | |
| 51 | 1 | $1.9 \times 10^5$ | $1.0 \times 10^4$ | 0 | 0 |

Mixture D, 16% NaPT, 2% ZnCl2, 20% monoethanolamine, 20% 3-amino-1-propanol. Mixture D was added to 12.5 L of semi-synthetic metalworking fluid to a final concentration of 1250 PPM, yielding final concentrations of 200 PPM active NaPT, 25 PPM ZnCl$_2$, 250 PPM monoethanolamine, 250 PPM 3-amino-1-propanol.

As shown in Table 2, the tank treated with mixture D showed at least 200-fold fewer bacteria in the bulk fluid than the untreated tank. There was little difference between treated and untreated tanks for the numbers of fungi in the bulk fluid. There was at least 1000-fold to 3000-fold fewer bacteria and at least 25-fold to 250-fold few fungi present in the biofilms of the tank treated with mixture D than the untreated tank. Although 10$^5$ bacteria/ml were present per ml of slime material from the air-fluid interface of the untreated tank, no bacteria or fungi could be detected from the slime material in the tank treated with mixture D.

Example 52

Biocidal Efficacy of a Mixture of Sodium Pyrithione, ZnCl$_2$, an Amine, and a Formaldehyde Releasing Biocide Against Microorganisms in Metalworking Fluids Experiments were performed to compare the biocidal efficacy of mixtures of sodium pyrithione, ZnCl$_2$, monoethanolamine, and hexahydro-1,3,5-tris(2-hydroxyethyl)-s-triazine (a formaldehyde releasing agent) with mixtures of sodium pyrithione and hexahydro-1,3,5-tris(2-hydroxyethyl)-s-triazine in metalworking fluids.

Sterile glass culture tubes (16 mm×150 mm) containing 3 ml of 5% soluble oil MWF or 5% semi-synthetic metalworking fluid were set up. To the tubes, 40% sodium pyrithione, 78.5% hexahydro-1,3,5-tris(2-hydroxyethyl)-s-triazine, or Mixture A (10% sodium pyrithione, 1.8% $ZnCl_2$ and 60.5% monoethanolamine) were added in appropriate amounts to create various mixtures of the biocides and controls for each of the biocides. Bacteria and fungi were added to each tube to total final concentrations of $10^7$ bacteria/ml and $10^5$ fungal spores/ml, respectively. The bacterial innoculum consisted of an equal number of cells from *Pseudomonas aeruginosa*, *Escherichia coli*, *Pseudomonas fluorescens*, *Pseudomonas rubescens*, and *Pseudomonas putida*. Fungal additions were composed of equal numbers of spores from *Fusarium* sp and *Cephalosporium* sp. Tubes were incubated at 28° C. for three days, and then were sampled for viable bacterial counts on Tyrptic Soy Agar plus 90 PPM cycloheximide and viable fungal counts on Malt Agar plus 900 PPM Streptomycin plus 550 PPM Penicillin G. Experimental results are shown in Table 3.

TABLE 3

Biocidal Efficacy of a Mixture of sodium pyrithione, $ZnCl_2$, Monoethanolamine and hexahydro-1,3,5-tris(2-hydroxyethyl)-s-triazine Against Microorganisms in Metalworking Fluids.

| Tube | NaPT (PPM ai NaPT) | Mixture A (PPM ai NaPT) | Triazine (PPM ai TZ) | Day 3 Bact/ml | Day 3 Fungi/ml |
|---|---|---|---|---|---|
| | | | | | |
| | | Experiment A: Soluble oil MWF | | | |
| 1 | 100 | 0 | 0 | $9.3 \times 10^6$ | $7.7 \times 10^4$ |
| 2 | 100 | 0 | 49 | 0 | $1.5 \times 10^4$ |
| 3 | 100 | 0 | 98 | 0 | $3.0 \times 10^3$ |
| 4 | 100 | 0 | 196 | 0 | 120 |
| 5 | 100 | 0 | 393 | 0 | 0 |
| 6 | 100 | 0 | 589 | 0 | 0 |
| 7 | 100 | 0 | 785 | 0 | 0 |
| 8 | 0 | 100 | 0 | 0 | 0 |
| 9 | 0 | 100 | 49 | 0 | 0 |
| 10 | 0 | 100 | 98 | 0 | 0 |
| 11 | 0 | 100 | 196 | 0 | 0 |
| 12 | 0 | 100 | 393 | 0 | 0 |
| 13 | 0 | 100 | 589 | 0 | 0 |
| 14 | 0 | 100 | 785 | 0 | 0 |
| 15 | 0 | 50 | 0 | 0 | 0 |
| 16 | 0 | 50 | 49 | 0 | 0 |
| 17 | 0 | 50 | 98 | 0 | 0 |
| 18 | 0 | 50 | 196 | 0 | 0 |
| 19 | 0 | 50 | 393 | 0 | 0 |
| 20 | 0 | 50 | 589 | 0 | 0 |
| 21 | 0 | 50 | 785 | 0 | 0 |
| 22 | 0 | 25 | 0 | 0 | $7.0 \times 10^3$ |
| 23 | 0 | 25 | 49 | 0 | $3.0 \times 10^3$ |
| 24 | 0 | 25 | 98 | 0 | $4.0 \times 10^3$ |
| 25 | 0 | 25 | 196 | 0 | 0 |
| 26 | 0 | 25 | 393 | 0 | 0 |
| 27 | 0 | 25 | 589 | 0 | 0 |
| 28 | 0 | 25 | 785 | 0 | 0 |
| 29 | 0 | 0 | 0 | $9.5 \times 10^6$ | $4.1 \times 10^4$ |
| 30 | 0 | 0 | 49 | $5.0 \times 10^5$ | $3.0 \times 10^3$ |
| 31 | 0 | 0 | 98 | $7.6 \times 10^4$ | $1.1 \times 10^3$ |
| 32 | 0 | 0 | 196 | 0 | 100 |
| 33 | 0 | 0 | 393 | 0 | 0 |
| 34 | 0 | 0 | 589 | 0 | 0 |
| 35 | 0 | 0 | 785 | 0 | 0 |
| | | Experiment B: Semi-Synthetic MWF | | | |
| 1 | 100 | 0 | 0 | $1.7 \times 10^6$ | $4.1 \times 10^4$ |
| 2 | 100 | 0 | 49 | 0 | $1.1 \times 10^4$ |
| 3 | 100 | 0 | 98 | 0 | $2.0 \times 10^3$ |
| 4 | 100 | 0 | 196 | 0 | 40 |
| 5 | 100 | 0 | 393 | 0 | 0 |
| 6 | 100 | 0 | 589 | 0 | 0 |
| 7 | 100 | 0 | 785 | 0 | 0 |
| 8 | 0 | 100 | 0 | 0 | 0 |
| 9 | 0 | 100 | 49 | 0 | 0 |
| 10 | 0 | 100 | 98 | 0 | 0 |
| 11 | 0 | 100 | 196 | 0 | 0 |
| 12 | 0 | 100 | 393 | 0 | 0 |
| 13 | 0 | 100 | 589 | 0 | 0 |
| 14 | 0 | 100 | 785 | 0 | 0 |
| 15 | 0 | 50 | 0 | 0 | 670 |
| 16 | 0 | 50 | 49 | 0 | 140 |
| 17 | 0 | 50 | 98 | 0 | 0 |
| 18 | 0 | 50 | 196 | 0 | 0 |
| 19 | 0 | 50 | 393 | 0 | 0 |
| 20 | 0 | 50 | 589 | 0 | 0 |
| 21 | 0 | 50 | 785 | 0 | 0 |
| 22 | 0 | 25 | 0 | 0 | $4.0 \times 10^3$ |
| 23 | 0 | 25 | 49 | 0 | $1.2 \times 10^3$ |
| 24 | 0 | 25 | 98 | 0 | 610 |
| 25 | 0 | 25 | 196 | 0 | 0 |
| 26 | 0 | 25 | 393 | 0 | 0 |
| 27 | 0 | 25 | 589 | 0 | 0 |
| 28 | 0 | 25 | 785 | 0 | 0 |
| 29 | 0 | 0 | 0 | $8.0 \times 10^5$ | $4.0 \times 10^3$ |
| 30 | 0 | 0 | 49 | 0 | $2.0 \times 10^3$ |
| 31 | 0 | 0 | 98 | 0 | 840 |
| 32 | 0 | 0 | 196 | 0 | 30 |
| 33 | 0 | 0 | 393 | 0 | 0 |
| 34 | 0 | 0 | 589 | 0 | 0 |
| 35 | 0 | 0 | 785 | 0 | 0 |

NaPT, Sodium pyrithione
Mixture A = 10% Sodium pyrithione, 1.8% $ZnCl_2$, 60.5% monoethanolamine;
TZ, Triazine = 78.5% Hexahydro-1,3,5-tris(2-hydroxyethyl)-s-triazine.

In Table 3, it should be noted that the Triazine used is a 78.5% aqueous solution of hexahydro-1,3,5-tris(2-hydroxyethyl)-s-triazine. It is known that hexahydro-1,3,5-tris(2-hydroxyethyl)-s-triazine is in equilibrium with free formaldehyde and typically releases about 31% formaldehyde when used as a formaldehyde releasing agent in metalworking fluids at in use concentrations. The relationship between triazine, hexahydro-1,3,5-tris(2-hydroxyethyl)-s-triazine, and formaldehyde in Examples 52, 53, and 54 is shown in Table 4:

TABLE 4

Relationship between Triazine, Hexahydro-1,3,5-tris(2-hydroxyethyl)-s-triazine, and Formaldehyde

| Triazine (PPM) | Hexahydro-1,3,5-tris (2-hydroxyethyl)-s-triazine (PPM) | Formaldehyde (PPM) |
|---|---|---|
| 63 | 49 | 20 |
| 125 | 98 | 40 |
| 250 | 196 | 80 |
| 500 | 392 | 160 |
| 750 | 589 | 240 |
| 1000 | 785 | 320 |
| 2000 | 1570 | 640 |

The experimental results shown in Table 3 illustrate that mixtures of Mixture A (10% Sodium pyrithione, 1.8% $ZnCl_2$, 6.0.5% monoethanolamine) and hexahydro-1,3,5-tris(2-hydroxyethyl)-s-triazine perform better against fungi than mixtures of sodium pyrithione and hexahydro-1,3,5-tris(2-hydroxyethyl)-s-triazine. For example, about 75% less active sodium pyrithione is required when Mixture A is used in conjunction with 250 to 500 PPM of hexahydro-1,3,5-tris(2-hydroxyethyl)-s-triazine to produce a biocidal efficacy comparable to that of mixtures of sodium pyrithione and 250 to 500 PPM of hexahydro-1,3,5-tris(2-hydroxyethyl)-s-triazine. Furthermore, increasing the concentration of Mixture A also permits reductions in the amounts of hexahydro-1,3,5-tris(2-hydroxyethyl)-s-triazine needed to eliminate fungal growth. For example, 500 PPM of Mixture A can reduce the amount of hexahydro-1,3,5-tris(2-hydroxyethyl)-s-triazine required to reduce fungi levels by 4-fold. When Mixture A is used at concentrations of about 1000 PPM, no hexahydro-1,3,5-tris(2-hydroxyethyl)-s-triazine is required to eliminate the microbial contamination.

Example 53

Efficacy of a Mixture of Sodium Pyrithione, ZnCl$_2$, Monoethanolamine and a Formaldehyde Releasing Biocide at Preventing Microbial Contamination in a Metalworking Fluid The efficacy of a mixture of sodium pyrithione, ZnCl$_2$, monoethanolamine and hexahydro-1,3,5-tris(2-hydroxyethyl)-s-triazine at preventing microbial contamination of a metalworking fluid was examined. Effectiveness was compared to the efficacy of a mixture of sodium pyrithione and hexahydro-1,3,5-tris(2-hydroxyethyl)-s-triazine.

Sterile 250 ml Erylenmeyer flasks containing 100 ml of 5% semi-synthetic metalworking fluid were set up. To the flasks, 40% sodium pyrithione, 78.5% hexahydro-1,3,5-tris(2-hydroxyethyl)-s-triazine, or Mixture A (10% sodium pyrithione, 1.8% ZnCl$_2$ and 60.5% monoethanolamine) were added in the appropriate amounts to create mixtures of the biocides and controls for each of the biocides. Bacteria and fungi were added to each flask to total final concentrations of $10^7$ bacteria/ml and $10^5$ fungal spores/ml, respectively. The bacterial innoculum consisted of an equal number of cells from *Pseudomonas aeruginosa*, *Escherichia coli*, *Pseudomonas fluorescens*, *Pseudomonas rubescens*, and *Pseudomonas putida*. Fungal additions were composed of equal numbers of spores from *Fusarium* sp and *Cephalosporium* sp. Bacterial and fungal challenges were repeated three times per week. Flasks were incubated at 28° C. and were sampled after several weeks for viable bacterial counts on Tryptic Soy Agar plus 90 PPM cycloheximide and viable fungal counts on Malt Agar plus 900 PPM Streptomycin plus 550 PPM Penicillin G. Experimental results are shown in Table 5.

TABLE 5

Prevention of Bacterial and Fungal Contamination of a Metalworking Fluid by Mixtures of NaPT, ZnCl$_2$, Monethanolamine, and a Formaldehyde Releasing Biocide.
Semi-synthetic MWF

| Flask | NaPT (ai NaPT) (PPM) | Mixture A (ai NaPT) (PPM) | Triazine (ai TZ) (PPM) | Bacteria/ml Week 4 | Bacteria/ml Week 9 | Fungi/ml Week 4 | Fungi/ml Week 9 |
|---|---|---|---|---|---|---|---|
| 1 | 100 | 0 | 0 | $3.2 \times 10^6$ | $6.1 \times 10^6$ | $8.9 \times 10^4$ | $5.6 \times 10^4$ |
| 2 | 0 | 100 | 0 | 0 | 0 | 0 | 40 |
| 3 | 0 | 50 | 0 | 0 | $6.0 \times 10^3$ | 380 | $1.6 \times 10^4$ |
| 4 | 0 | 25 | 0 | 0 | $1.1 \times 10^7$ | $6.0 \times 10^3$ | $3.6 \times 10^4$ |
| 5 | 0 | 0 | 0 | $4.8 \times 10^6$ | $4.9 \times 10^6$ | $1.0 \times 10^4$ | $5.3 \times 10^4$ |
| 6 | 100 | 0 | 196 | 0 | $1.2 \times 10^6$ | 610 | $4.3 \times 10^4$ |
| 7 | 0 | 100 | 196 | 0 | 0 | 0 | 0 |
| 8 | 0 | 50 | 196 | 0 | 0 | 0 | 100 |
| 9 | 0 | 25 | 196 | 0 | $3.0 \times 10^3$ | 0 | $5.0 \times 10^3$ |
| 10 | 0 | 0 | 196 | $2.0 \times 10^5$ | $1.0 \times 10^7$ | $3.6 \times 10^4$ | $6.2 \times 10^4$ |
| 11 | 100 | 0 | 393 | 0 | 30 | 50 | 0 |
| 12 | 0 | 100 | 393 | 0 | 0 | 510 | 0 |
| 13 | 0 | 50 | 393 | 0 | 0 | 0 | 0 |
| 14 | 0 | 25 | 393 | 0 | 0 | 0 | 0 |
| 15 | 0 | 0 | 393 | 0 | 160 | 0 | 70 |
| 16 | 100 | 0 | 785 | 0 | 0 | 0 | 0 |
| 17 | 0 | 100 | 785 | 0 | 0 | 0 | 0 |
| 18 | 0 | 50 | 785 | 0 | 0 | 0 | 0 |
| 19 | 0 | 25 | 785 | 0 | 0 | 0 | 0 |
| 20 | 0 | 0 | 785 | 0 | 0 | 0 | 0 |

NaPT = Sodium pyrithione

Mixture A = 10% Sodium pyrithione, 1.8% ZnCl$_2$, 60.5% monoethanolamine;

TZ, Triazine = 78.5% Hexahydro-1,3,5-tris(2-hydroxyethyl)-s-triazine.

In this semi-synthetic fluid, mixtures of Mixture A and hexahydro-1,3,5-tris(2-hydroxyethyl)-s-triazine provide a longer duration of protection from microbial contamination than mixtures of NaPT and hexahydro-1,3,5-tris(2-hydroxyethyl)-s-triazine. Furthermore, Mixture A and hexahydro-1,3,5-tris(2-hydroxyethyl)-s-triazine mixtures also permit the use of less sodium pyrithione or less hexahydro-1,3,5-tris(2-hydroxyethyl)-s-triazine than mixtures of sodium pyrithione and hexahydro-1,3,5-tris(2-hydroxyethyl)-s-triazine while retaining the same duration of efficacy.

Example 54

Effects of Iron Ions on the Discoloration and Biocidal Efficacy a Mixture of Sodium Pyrithione, $ZnCl_2$, and an Amine in Metalworking Fluid The presence of iron ions is known to cause blue discoloration of metalworking fluids containing sodium pyrithione. Furthermore, iron ions also reduce the biocidal efficacy of sodium pyrithione. An experiment was conducted to examine whether a mixture of sodium pyrithione, $ZnCl_2$, and monoethanolamine would similarly show lower efficacy against microorganisms and produce blue discoloration in the presence of iron.

Sterile 250 ml Erylenmeyer flasks with cheesecloth stoppers were filled with 100 ml of 5% metalworking fluids. The fluids examined included a soluble oil, two semi-synthetics, and a synthetic. The water used to construct the 5% fluids contained various concentrations of Fe ions ($FeCl_3.6H_2O$) ranging from 0 PPM to 200 PPM. Mixture A, composed of 10% NaPT, 1.8% $ZnCl_2$, and 60.5% monoethanolamine, was added to the appropriate flasks at final concentrations of 1000 PPM, yielding final active concentrations of NaPT and Zn (II) of 100 PPM and 8.6 PPM, respectively, in the fluids. Untreated controls and controls treated with 100 ai PPM NaPT only were also established. Three times per week, bacteria and fungi were added the flasks to total final concentrations of $10^7$ bacteria/ml and $10^5$ fungal spores/ml. Bacterial additions were composed of an equal number of cells for *Pseudomonas aeruginosa* 9027, *Escherichia coli* 8739, *Pseudomonas fluorescens* 12201, *Pseudomonsa rubescens* 12202, and *Pseudomonas putida*. The fungal challenge consisted of equal numbers of spores of *Fusarium* sp. and *Cephalosporium* sp. Flasks were incubated on a shaker at room temperature (23° C.±2° C.) and at 120 rpms. Initial color of the metalworking fluids was determined by visual inspection. At two weeks, bacterial and fungal viable counts were determined by plating on Tryptic Soy Agar containing 90 PPM cycloheximide and Malt Agar containing 900 PPM Streptomycin and 550 PPM Penicillin G, respectively. Color of fluids was examined. Experimental results are shown in Table 6.

TABLE 6

Effects of Iron Ions on the Discoloration and Biocidal Efficacy a Mixture of sodium pyrithione, $ZnCl_2$, and Monoethaolamine in Metalworking Fluid.

| Flask | 40% NaPT (ai NaPT) (PPM) | Mixture A (ai NaPT) (PPM) | Initial Fe(III) (PPM) | Blue Color | Week 2 Bacterial/ml | Fungi/ml |
|---|---|---|---|---|---|---|
| A. Soluble oil MWF |||||||
| 1 | 0 | 0 | 0 | no | $1.5 \times 10^7$ | $1.5 \times 10^5$ |
| 2 | 100 | 0 | 100 | light blue | $1.4 \times 10^7$ | $1.5 \times 10^5$ |
| 3 | 0 | 100 | 0 | no | 0 | 30 |
| 4 | 0 | 100 | 50 | no | 100 | 80 |
| 5 | 0 | 100 | 100 | no | 60 | 60 |
| 6 | 0 | 100 | 200 | light blue | $1.2 \times 10^7$ | $2.0 \times 10^3$ |
| B. Semi-synthetic MWF |||||||
| 7 | 0 | 0 | 0 | no | $7.7 \times 10^6$ | $8.0 \times 10^4$ |
| 8 | 100 | 0 | 100 | dark blue | $1.1 \times 10^7$ | $5.9 \times 10^4$ |
| 9 | 0 | 100 | 0 | no | 0 | 0 |
| 10 | 0 | 100 | 50 | darkblue | 0 | 0 |
| 11 | 0 | 100 | 100 | dark blue | 0 | 0 |
| 12 | 0 | 100 | 200 | dark blue | $2.6 \times 10^4$ | $1.2 \times 10^3$ |
| C. Semi-synthetic MWF |||||||
| 13 | 0 | 0 | 0 | no | $7.0 \times 10^5$ | $1.3 \times 10^3$ |
| 14 | 100 | 0 | 100 | blue | $1.2 \times 10^6$ | $1.8 \times 10^3$ |
| 15 | 0 | 100 | 0 | no | 0 | 0 |
| 16 | 0 | 100 | 50 | no | 0 | 0 |
| 17 | 0 | 100 | 100 | no | 0 | 0 |
| 18 | 0 | 100 | 200 | no | 0 | 0 |
| D. Synthetic MWF |||||||
| 19 | 0 | 0 | 0 | no | $2.1 \times 10^6$ | $4.0 \times 10^3$ |
| 20 | 100 | 0 | 100 | light blue | $5.0 \times 10^5$ | $4.0 \times 10^3$ |
| 21 | 0 | 100 | 0 | no | 0 | 0 |
| 22 | 0 | 100 | 50 | no | 0 | 0 |
| 23 | 0 | 100 | 100 | no | 0 | 0 |
| 24 | 0 | 100 | 200 | light blue | 0 | 0 |

NaPT = sodium pyrithione
Mixture A = 10% sodium pyrithione ai., 1.8% Zncl$_2$, 60.5% monoethanolamine;
Fe(III) = Fecl$_3$.6H$_2$0

The results in Table 6 indicated that Mixture A is generally much less susceptible to producing blue discoloration in metalworking than NaPT. Although the blue color intensity varied among the fluids, no bluing was observed in three of the four fluids containing up to 100 PPM Fe ions. At 200 PPM Fe, three of the fluids showed some blue color. One fluid, however, demonstrated no blue color even in the presence of 200 PPM Fe ions. Results also showed that biocidal efficacy against bacteria and fungi was little effected by Fe ions at concentrations of 100 PPM or less. In two of the four fluids, efficacy was reduced when 200 PPM Fe ions were present. The remaining two fluids showed no change in efficacy.

Example 55

Preparation of Stable, Soluble, Concentrated Mixtures of Sodium Pyrithione, Zinc Chloride and Organic Amines Mixtures of sodium pyrithione, $ZnCl_2$ and various organic amines were set up in 100 ml clear glass bottles and were placed at room temperature (23° C.±2° C.). Mixtures were scored for the presence or absence of a precipitate or any other indication of physical instability at 24 hours and 72 hours post construction.

TABLE 7

Solubility and Stability of Mixtures of Sodium Pyrithione, Zinc Chloride and Organic Amines (Including Single Amines [see Part A] and Mixtures of Amines [see Part B])

| Mixture | Weight % | Appearance at 24 Hrs | Appearance at 72 Hrs |
|---|---|---|---|
| PART A - SINGLE AMINES | | | |
| NaPT | 10.00 | | |
| $ZnCl_2$ | 1.74 | | |
| Organic Amine | 60.50 | | |
| Water | 27.76 | | |
| 1, 2 and 1, 3 ALKANOLAMINES: FORMULA 1 | | | |
| Ethanolamine $NH_2-CH_2-CH_2-OH$ | 60.50 | S | S |
| 1-Amino-2-Propanol | 60.50 | S | S |
| 3-Amino-1-Propanol $NH_2-CH-CH_2-CH_2-OH$ | 60.50 | S | S |
| 2-(methylamino)ethanol $CH_3-NH_2-CH_2-CH_2-OH$ | 60.50 | S | S |
| Propylethanol amine $CH_3-CH_2-CH_2-NH-CH_2-CH_2-OH$ | 60.50 | S | P |
| 1, 2 and 1, 3 ALKANOLANINES: FORMULA 2 | | | |
| Diethanolamine $HO-CH_2-CH_2-NH-CH_2-CH_2-OH$ | 60.50 | P | P |
| Triethanolamine | 60.50 | P | P |
| 2-Amino-2-methyl-1-propanol | 60.50 | P | P |
| 2-Amino-2-ethyl-1,3-propanediol | 60.50 | P | P |
| 2(2-Aminoethoxy) ethanol $NH_2-CH_2-CH_2-O-CH_2-CH_2-OH$ | 60.50 | P | P |
| n-Methyldiethanolamine | 60.50 | P | P |
| n,n-Dimethylethanolamine | 60.50 | P | P |

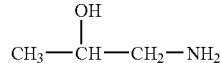
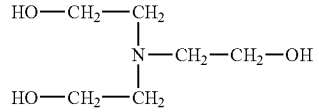
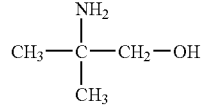
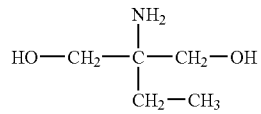
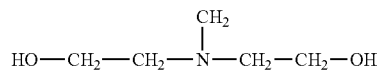
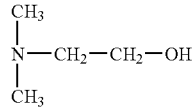

TABLE 7-continued

Solubility and Stability of Mixtures of Sodium Pyrithione, Zinc Chloride and Organic Amines (Including Single Amines [see Part A] and Mixtures of Amines [see Part B])

| Mixture | Weight % | Appearance at 24 Hrs | Appearance at 72 Hrs |
|---|---|---|---|
| n,n-Diethylethanolamine | 60.50 | P | P |

$$CH_2-CH_3$$
$$|$$
$$N-CH_2-CH_2-OH$$
$$|$$
$$CH_2-CH_3$$

| Mixture | Weight % | Appearance at 24 Hrs | Appearance at 72 Hrs |
|---|---|---|---|
| Diisopropanolamine | 60.50 | P | P |

$$\begin{array}{c} & & & & CH_3 \\ & & & & | \\ HO-CH-CH_2-NH-CH_2-CH-OH \\ | \\ CH_3 \end{array}$$

| Mixture | Weight % | Appearance at 24 Hrs | Appearance at 72 Hrs |
|---|---|---|---|
| Triisopropanolamine | 60.50 | P | P |

$$\begin{array}{c} & & & & CH_3 \\ & & & & | \\ HO-CH-CH_2-NH-CH_2-CH-OH \\ | & & | \\ CH_3 & & CH_2-CH-OH \\ & & | \\ & & CH_3 \end{array}$$

| Mixture | Weight % | Appearance at 24 Hrs | Appearance at 72 Hrs |
|---|---|---|---|
| Mixed Isopropanolamines (44% Di, 44% Tri and 12% Mono) | 60.50 | S | P |
| ALKYLDIAMINES: FORMULA 3 | | | |
| 1,3-Diaminopropane $NH_2-CH_2-CH_2-CH_2-NH_2$ | 60.50 | S | S |
| Diethylenetriamine $NH_2-CH_2-CH_2-NH-CH_2-CH_2-NH_2$ | 60.50 | S | S |
| Triethylenetetraamine $NH_2(CH_2-CH_2-NH)_3-H$ | 60.50 | S | S |
| Polyethylene imine $NH_2(CH_2-CH_2-NH)n-H$ | 60.50 | S | S |
| PART B - AMINES MIXTURES | | | |
| NaPT | 10.00 | | |
| $ZnCl_2$ | 1.74 | | |
| Organic Amines | 60.50 | | |
| Water | 27.76 | | |
| 1, 2 and 1, 3 ALKANOLAMINES: FORMULA 1 + FORMULA 2 | | | |
| Ethanolamine | 30.00 | S | S |
| 2-Amino-2-methyl-1-propanol | 30.50 | | |
| Ethanolamine | 20.00 | S | S |
| 2-Amino-2-methyl-1-propanol | 40.50 | | |
| Ethanolamine | 10.00 | P | P |
| 2-Amino-2-methyl-1-propanol | 50.50 | | |
| Ethanolamine | 20.00 | S | S |
| Diethanolamine | 40.50 | | |
| Ethanolamine | 20.00 | S | S |
| Triethanolamine | 40.50 | | |
| Ethanolamine | 20.00 | S | S |
| 2-Amino-2-ethyl-1,3-propanediol | 40.50 | | |
| Ethanolamine | 20.00 | P | P |
| Diglycol amine | 40.50 | | |

P = precipitate formed in mixture
S = soluble, stable mixture

As shown in table 7, soluble and stable mixtures were observed after 24 and 72 hours using 1-amino-2-propanol, 3-amino-1-propanol, 2-(methylamino)ethanol, 1,3-diaminopropane, diethylenetriamine, ethanolamine, triethylenetetraamine, and polyethylene imine. Three amines propylethanolamine, mixed isopropanolamines, and 3-methoxypropylamine) showed soluble mixtures after 24 hours but not after 72 hours. AMP 95, diethanolamine, AEPD 85, 2(2-aminoethoxy)ethanol, N-methyldiethanolamine, N,N-dimethylethanolamine, N,N-diethylethanolamine, triethanolamine, ethylenediamine, triethylamine, triisopropanolamine, and diisopropanolamine showed precipitates after 24 and 72 hours. Part B of Table 7 demonstrates that certain amine mixtures provide suitable solubility when employed in combination.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A method for inhibiting the growth of free-living microorganisms or biofilm in a metalworking fluid, comprising the steps of:
   (A) providing an antimicrobial composition concentrate comprising: (a) from about 1% to about 10% of sodium pyrithione; (b) from about 0.05 to about 3% of a zinc source selected from the group consisting of zinc salts, zinc borates, zinc oxides, zinc hydroxides, zinc sulfates, zinc chlorides, zinc alloys, zinc complexes, and combinations thereof; (c) from about 40% to 70% of alkanolamines selected from the group consisting of ethanolamine, 1-amino-2-propanol, 3-amino-l-propanol, and combinations thereof;
   (B) incorporating said antimicrobial composition concentrate into a metalworking fluid to to provide a "masterbatch" comprising, fluid,
      (a) from about 0.05 to about 5% sodium pyrithione;
      (b) from about 0.005 to about 1% of said zinc source;
      (c) from about 0.5 to about 40% of said alkanol amines;
   (C) diluting said "masterbatch" to produce an antimicrobially effectively metal working fluid,
   (D) contacting said free-living microorganisms or biofilm with said antimicrobially effective metalworking fluid,
wherein said antimicrobially effective metalworking fluid has an enhanced biocidal effect against free-living microorganisms or biofilms.

2. The method of claim 1, wherein said zinc salt is selected from the group consisting of zinc acetate, zinc borate, zinc oxide, zinc carbonate, zinc chloride, zinc-sulfate, zinc hydroxide, zinc citrate, zinc fluoride, zinc iodide, zinc lactate, zinc oleate, zinc oxalate, zinc phosphate, zinc propionate, zinc salicylate, zinc selenate, zinc silicate, zinc stearate, zinc sulfide, zinc tannate, zinc tartrate, zinc valerate, and combinations thereof.

3. The method of claim 1, wherein said free-living microorganism or biofilm comprises a microbial component selected from the group consisting of gram positive bacteria, gram negative bacteria, yeasts, fungi, and combinations thereof.

4. The method of claim 1 wherein said microbial component is selected from the group consisting of *Pseudomonas aeruginosa, Aspergillus niger, Fusarim, Cephalosporium, Pseudomonas fluorescens, Pseudomonas rubescens, Pseudomonas stutzeri, Pseudomonas olevorans, Alcaligenes faecalis, Citrobacter freundii, Escherichia coli*, and combinations thereof.

5. The method of claim 1, wherein the antimicrobial composition concentrate further comprises from about 0.1 to about 30 wt% of a formaldehyde.

6. The method of claim 5, wherein said formaldehyde source is selected from the group consisting of formaldehyde, cis 1-(3-chloroallyl)-3,5,7-triaza-l-azoniaadamantane chloride, hexahydro-1 ,3,5-tris (2-hydroxyethyl)-s-triazine, 4,4-dimethyloxazolidine, 5-hydroxymethoxymethyl-1-1 aza-3, 7 -dioxabicyclo-octane, dimethyloldimethyldantoin, N,N"-methylene bis [N'-[hydroxymethyl)-2,5-dioxo-4-imidazolidinyl]urea], N -(hydroxymethyl)-N(1,3-dihydroxymethyl-2,5-dioxo-4-imidazolidinyl)-N'-(hydroxymethyl) urea, hexahydro-1,3,5-tris (2-hydroxyethyl)-s-triazine, and combinations thereof.

7. A method of using an antimicrobial composition which comprises incorporating said antimicrobial composition into a metalworking fluid in order to impart antimicrobial efficacy to said metalworking fluid, wherein said antimicrobial composition comprises: from about 0.05 to about 5% sodium pyrithione; from about 0.005 to about 1% of a zinc source selected from the group consisting of zinc salts, zinc borates, zinc oxides, zinc hydroxides, zinc sulfates, zinc chlorides, zinc alloys, zinc complexes, and combinations thereof; and from about 0.5 to about 40% of an organic amine component selected from a group consisting of selected from the group consisting of ethanolamine, 1-amino-2-propanol, 3-amino-l-propanol, and combinations thereof.

* * * * *